US009672618B1

(12) United States Patent
Hassanain et al.

(10) Patent No.: US 9,672,618 B1
(45) Date of Patent: Jun. 6, 2017

(54) SYSTEM AND PROCESS FOR DYSLEXIA SCREENING AND MANAGEMENT

(71) Applicants: Elham Mahjoob Hassanain, Riyadh (SA); Mohamed Abdur Rahman, Makkah (SA); Salaheldin Hassanain, Riyadh (SA)

(72) Inventors: Elham Mahjoob Hassanain, Riyadh (SA); Mohamed Abdur Rahman, Makkah (SA); Salaheldin Hassanain, Riyadh (SA)

(73) Assignees: Elham Mahjoob Hassanain (SA); Mohamed Abdur Rahman (SA); Salaheldin Hassanain (SA)

( * ) Notice: Subject to any disclaimer, the term of this patent is extended or adjusted under 35 U.S.C. 154(b) by 0 days.

(21) Appl. No.: 15/237,591

(22) Filed: Aug. 15, 2016

(51) Int. Cl.
| | |
|---|---|
| *G09B 5/00* | (2006.01) |
| *G06T 7/00* | (2017.01) |
| *G06K 9/00* | (2006.01) |
| *G06K 9/52* | (2006.01) |
| *G06T 7/20* | (2017.01) |
| *A61B 3/113* | (2006.01) |
| *A61B 5/11* | (2006.01) |
| *A61B 5/16* | (2006.01) |
| *G10L 25/66* | (2013.01) |

(52) U.S. Cl.
CPC ............ *G06T 7/0012* (2013.01); *A61B 3/113* (2013.01); *A61B 5/11* (2013.01); *A61B 5/16* (2013.01); *G06K 9/00335* (2013.01); *G06K 9/00617* (2013.01); *G06K 9/52* (2013.01); *G06T 7/20* (2013.01); *G06T 2207/30196* (2013.01); *G10L 25/66* (2013.01)

(58) Field of Classification Search
None
See application file for complete search history.

(56) References Cited

U.S. PATENT DOCUMENTS

| | | | | |
|---|---|---|---|---|
| 8,465,288 | B1 * | 6/2013 | Roers ................... | G09B 7/00 434/118 |
| 8,897,437 | B1 * | 11/2014 | Tan ..................... | H04M 3/5175 379/265.02 |
| 2005/0257146 | A1 * | 11/2005 | Ashcraft .............. | G06F 17/273 715/257 |
| 2006/0087510 | A1 * | 4/2006 | Adamo-Villani ....... | G06F 3/017 345/474 |
| 2015/0118661 | A1 * | 4/2015 | Haruta ................. | G09B 5/00 434/169 |

* cited by examiner

*Primary Examiner* — Tsung-Yin Tsai
(74) *Attorney, Agent, or Firm* — Geeta Kadambi; Riddhi IP LLC

(57) ABSTRACT

A Dyslexia screening and management system and process for individual user, community and group in general are described. An electronic media based tests for reading, writing, drawing, spelling and listening skills, family drawing, and letter writing test, which uses text, audio, video, and gaze movement to detect a set of symptoms of having dyslexia is described. Multi-modal, language-independent screening test modules have been developed, which gives indications of further dyslexia diagnosis tool. The multimedia retrieval framework is presented to accelerate and ease the process of testing dyslexia at the global level, and to identify and auto assess potential dyslexic patterns and to accumulate huge collection of multimedia test data for in-depth clinical dyslexia pattern analysis.

13 Claims, 47 Drawing Sheets

2802

2804

| Stroke | Characteristics | Numeric code |
|---|---|---|
| — | Horizontal line | 1 |
| ╱ | Positive sloping line | 2 |
| │ | Vertical line | 3 |
| ╲ | Negative sloping line | 4 |
| ⊂ | Vertical concave curve | 5 |
| ⊃ | Vertical convex curve | 6 |
| None | Rejected stroke | 0 |

| Input segments ↓ / Reference segments → | Rseg₁ | ………… | Rseg$_k$ |
|---|---|---|---|
| Iseg₁ | $S_{1,1}$ | | $S_{1,k}$ |
| Iseg₂ | $S_{2,1}$ | | $S_{2,k}$ |
| ⋮ | ⋮ | ………… | ⋮ |
| Iseg$_n$ | $S_{n,1}$ | | $S_{n,k}$ |

|   | Reference segment → |   |   |   |   |   |
|---|---|---|---|---|---|---|
|   | 1 | 2 | 3 | 4 | 5 | 6 |
| 1 | 100 | 50 | 5 | 50 | 5 | 5 |
| 2 | 50 | 100 | 50 | 0 | 70 | 0 |
| 3 | 5 | 50 | 100 | 50 | 10 | 10 |
| 4 | 50 | 0 | 50 | 100 | 0 | 70 |
| 5 | 5 | 70 | 10 | 0 | 100 | 0 |
| 6 | 5 | 0 | 10 | 70 | 0 | 100 |

(Input segment ↓)

|   | 5 | 3 | 6 | 5 |
|---|---|---|---|---|
| 5 | 100 | 10 | 0 | 100 |
| 3 | 10 | 100 | 10 | 10 |
| 3 | 10 | 100 | 10 | 10 |
| 6 | 0 | 10 | 100 | 0 |

|   | 0 | 4 | 5 | 3 |
|---|---|---|---|---|
| 5 | 0 | 100 | 10 | |
| 3 | 50 | 10 | 100 | |
| 3 | 50 | 10 | 100 | |
| 6 | 70 | 0 | 10 | |

*FIG. 44B*

SYSTEM AND PROCESS FOR DYSLEXIA SCREENING AND MANAGEMENT

FIELD OF TECHNOLOGY

The present invention relates generally to a system and process for language-independent dyslexia screening test results, analyzing the big data using a Dyslexia intelligent analytics engine and managing dyslexia within individual, group and community.

BACKGROUND

Dyslexia is a cognitive disability that hinders one in normal reading, writing and drawing texts and objects (Rello, I et. al. 2015). Although children with dyslexia tend to show gifted intelligence, the learning disability poses a great challenge to adapt to the normal learning styles in the school (Gagi, O et. al. 2012). Hence, dyslexic children need to be identified by the parents and the school administration so that special assisting technologies can be provided to them (Eshshan, H. M., et. al. (2012). Although various test mechanisms have been proposed in the past in finding the presence of dyslexia among children in preschool and junior schools (Bartolome, N. A. et. al. 2012, Costa, M et. al. 2013, Nur, S. S. et. al. 2014), most of them cannot be applied to a mass level or support one single modality of tests. Thanks to the recent advancements in multimedia technologies, tablet PCs, high speed Internet communication even at rural areas and big data analytics, to name a few, a new dimension of finding symptoms of dyslexia is now possible. There is need to create a solution to implement this test that is ubiquitous but also fits the individual needs.

SUMMARY

The present invention relates generally to a system and process for language-independent dyslexia screening test results, for individuals and they can be grouped as community and country results for screening for Dyslexia and predicting health outcomes for the society.

In one embodiment, a mobile device enabled system and process for Dyslexia screening and management is disclosed. In another embodiment, a Dyslexia system comprising of computer hardware, server, processor and software for a user to test their skills in writing, drawing and talking along with their eye tracking is captured and analyzed for doctors to treat. In one embodiment, a Dyslexia analytics system that is intelligent which includes processes and systems to collect, capture, classify, store, and manage dyslexia data, and dynamically analyze, process and report personalized metrics using such data are disclosed.

In one embodiment, when a user takes these tests the results are captured and specific equations such Equation 1 to 4 are implemented to calculate the results and results are used by the auto grading module to produce results automatically. The results may also be verified manually by producing results using doctor analyzer software to corroborate. In one embodiment, the system provides visibility and transparency about performance management to individual, school and group participants and may be used by healthcare and policy maker participants to guide them towards better health care outcomes for the community and country.

In one embodiment, intelligent Dyslexia analytics system provides the analytic engine to do real-time and forensic analysis of the data captured from individual users for dyslexia. The data is analyzed for individual, group, school and community and common metrics are measured. In another embodiment, expert system is introduced for the Dyslexia analytics system to be further analyzed by experts such as doctors and policy makers for checking the higher level value for health care, impact and investments.

In one embodiment, several test modules are used in multiple languages for the user to take their test. The test increase in complexity, are age dependent, school curriculum depended and may be tailored to the user level.

In one embodiment, a video is captured for registering the eye tracking movement for Dyslexic patients as that is one of the symptoms that is described by the physicians for diagnosis. In another embodiment, a user uses a test module housed on a server or a processor of a computer device used for logging in to take for Dyslexia, wherein the test module is at least one of a reading, writing, drawing, spelling and listening skills, family drawing, and letter writing test. In another embodiment, a backend server captures the interaction of the user for a session for a given test module by capturing the interaction and video captured during the test period. In yet another embodiment, Dyslexia analytics system that is intelligent is housed on a backend server or a processor to auto grade a test result using specific equation and augments the video data captured during the session for a reading, writing, drawing, spelling and listening skills, family drawing, and letter writing test; and a doctor to review the test result using a doctor analyzer screen and rendering their opinion to the user by filtering and flagging each test module that shows symptoms of dyslexia and a treatment plan for the user. The Dyslexia analytics system is called intelligent Dyslexia system because the system and process automatically captures, stores, analysis and presents the results as a comparative graph to the physician as a result for a given user. No manual intervention is done and all the calculations are done at the backend servers or processors and presented on a user interface.

In one embodiment, the test module is 20-minute long and has 4 different tests: reading test, writing test, clock drawing test, and cognitive test through drawing family members, all with an eye tracking and audio capturing capabilities.

The systems and process disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF DRAWINGS

The embodiments of this invention are illustrated by way of example and not limitation in the figures of the accompanying drawings, in which like references indicate similar elements and in which:

FIG. 43 illustrates the relative matching scores for specified dyslexic primitive codes.

FIGS. 44A and 44B illustrates the average dyslexic pattern matching scores.

Figure 1:
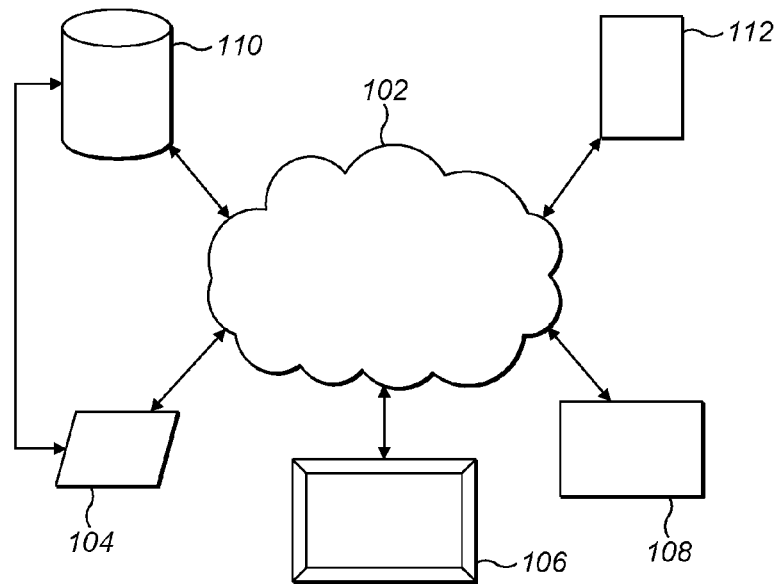
FIG. 1 is a block diagram of an example of a dyslexia screening and management system, according to one or more embodiments.

Other features of the present embodiments will be apparent from the detailed description that follows.

DETAILED DESCRIPTION

Several systems and process for informational, integrated and interactive Dyslexia testing modules using hardware that includes servers, mobile devices and software to screen for Dyslexia and to manage the outcome after the use by the user/individual by the doctors are disclosed. Although the present embodiments have been described with reference to specific example embodiments, it will be evident that various modifications and changes may be made to these embodiments without departing from the broader spirit and scope of the various embodiments.

In this work, a tablet PC based multimedia framework has been used where 4 different dyslexia testing modules, reading, writing, drawing and eye tracking have been proposed. The test can be administered by a school on a national level, where each individual test is graded by a licensed dyslexia therapist.

Each user interactions with the test modules are stored as a video along with the audio and gaze or pupil movement. At the end of a test session, the tablet PC communicates with the cloud based big data environment where the multimedia data consisting of user drawn text, user interaction with different test modules captured as an audio, video and screen images are uploaded for a set of methods to detect dyslexia phenomena. The methodology automatically detects dyslexia from the available multimedia files and shares the results with a dyslexia therapist for further analysis.

The test modules have been tested with a Samsung tablet, Samsung Galaxy Note 4, and a Microsoft Surface Pro 4 tablet PC with a stylus pen as support. In tablets and smartphones, we save images in .jpg format in 896*530 resolution and save video in .mp4 format. The video is created using FFMPEG codec library. Generally video size for 3 min is 30-50 KB with a rate of 30 frames per second.

We have developed a library, which can detect user drawn numbers from 1 to 12 and the position and angles of hour and minute hands of a clock. The library is built using python based open CV image processing library. KNN method is used for number and hand detection. Although at the current stage the library is working fine, but it lacks sufficient training data from actual testing modules. The more the training data we will have; the more accurate result will be produced by the analytics engine.

The eye tracking module has been implemented using Eyetribe with EyeTribe SDK version 0.9.56. The big data repository has been implemented using Amazon Infrastructure as a Service (IaaS). The Amazon EC2 instances allow quickly scaling capacity both up and down as the computing requirements changes, which is a fundamental case for our application due to variable usage. The API server is deployed on the EC2 instances where scaling and load balancing is configured by creating AWS Auto scaling Group, which is monitored and triggered when the average utilization of EC2 is high or low. This is done using the Cloud Watch for scaling activities. Elastic Load Balancing is used to distribute traffic to instances within Auto scaling Group to get the optimum utilization of the resources and cost. The media files are stored in Amazon S3 big data repository while the relational database that stores user profile, dyslexia profile, session metadata, and other relational data is implemented in PostGreSQL Database.

FIG. 1 is a block diagram of an example of a dyslexia screening system, according to one or more embodiments. Particularly, the system is supported by server 104, computing devices 106, 104, 108, and 112 (some, such as device 112, which may be mobile devices), a network 102, a database 110. In another embodiment, the user hard ware such as a PDA, computer or a mobile phone or any wireless device, or an electronic book (e-book) may be connected with each other or work independently to allow the user to use the multimedia tool for education and testing. A network 102 may be a local area network (LAN), wide area network (WAN), metropolitan area network (MAN), extranet, intranet, internet, peer-to-peer network or the like or a combination thereof. In the case of a wireless network, 102 may comprise, but need not be limited to HomeRF, Hiper-LAN, Bluetooth, Zigbee, WiMAX, Wibree, FM, AM, 802.11 (G, N), WiFi and satellite, Wireless ISP, Satellite Broadband, Mobile Broadband, Local Multipoint Distribution Service and satellite communication systems etc. In one embodiment, the system may be a server-client system with processing occurring on one or more computers or mobile devices connected through a network 102. In another embodiment, the system may be a peer-to-peer system with processing occurring in all computers or mobile devices connected through a network 102. In one embodiment, data is aggregated and stored in a central database server 110 connected to one or more computers or servers either directly or through a network 102. In another embodiment, data stores may be distributed among various devices and servers in the system.

Figure 2:
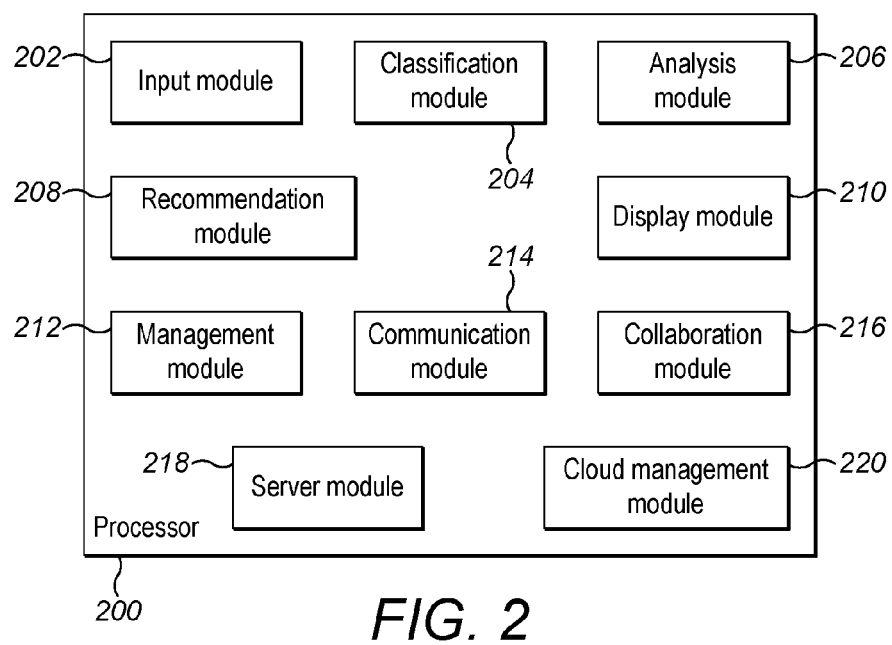
FIG. 2 is a block diagram illustrating the different modules within the management system to accomplish the gathering and analyzing of test results.

FIG. 2 is a block diagram illustrating the different modules that may reside in a processor or a server 200 for Dyslexia screening and management. Collectively the software represented as modules residing and processed by the hardware are input module 202, classification module 204, analysis module 206, recommendation module 208, display module 210, management module 212, communication module 214, collaboration module 216, server module 218 and cloud management module 220. Modules in FIG. 2 have interfaces to the users, and one-to-one connectivity to the backend intelligence. The modules in backend intelligence that provide active support and computation work based on stimuli from the blocks in FIG. 2. For example, the user interface for input module 202 receives user input and relays to intelligent Dyslexia analytics system 606 component User graphical user interface (GUI) management 1002. Similarly, classification module in 204 interfaces with back-end classification module 1006. Further information of back-end intelligence is provided in FIG. 10.

Various modules of the Dyslexia analytics system as a software resident in the computing device used by the end user who is taking the test are illustrated in FIG. 2. Input Module 202 may receive inputs from other systems within or external to the application, and from users and experts such as doctors. Classification Module 204 may contain system templates and may request data from other modules within the dyslexia test application to create associations among data using system templates. Analysis Module 206 may receive data from other modules and process that data to generate individual or aggregated performance metrics to be relayed to the backend intelligence through client interfaces. Recommendation Module 208 may calculate recommended performance goals or activities for that user or group based on results of classification and analysis to be relayed to the Dyslexia analytics system. Display Module 210 may present a user interface to a user to visually display results generated by the dyslexia test application. The display user interface may be interactive allowing the user to view, add, edit, configure, copy, store, remove, send or comment upon displayed results. In one embodiment, automatic performance review documentation uses these methods.

FIG. 2 also illustrates the client side management module 212 that manages the data acquired through user interfaces, to be collected and relayed to Dyslexia analytics system. Similarly, management module 212 also receives information from the Dyslexia analytics system to be displayed over user interfaces. Communication module 214 uses the network resources to communicate with the backend server and Dyslexia analytics system over network.

Collaboration module 216 maps the user to groups taking similar tests. Server module 218 uses the communication module 214 to reach its cohort in the Dyslexia analytics system for relaying the results. Cloud management module 220 interfaces the client side to the relational and NoSQL data bases in the server side.

Figure 3:
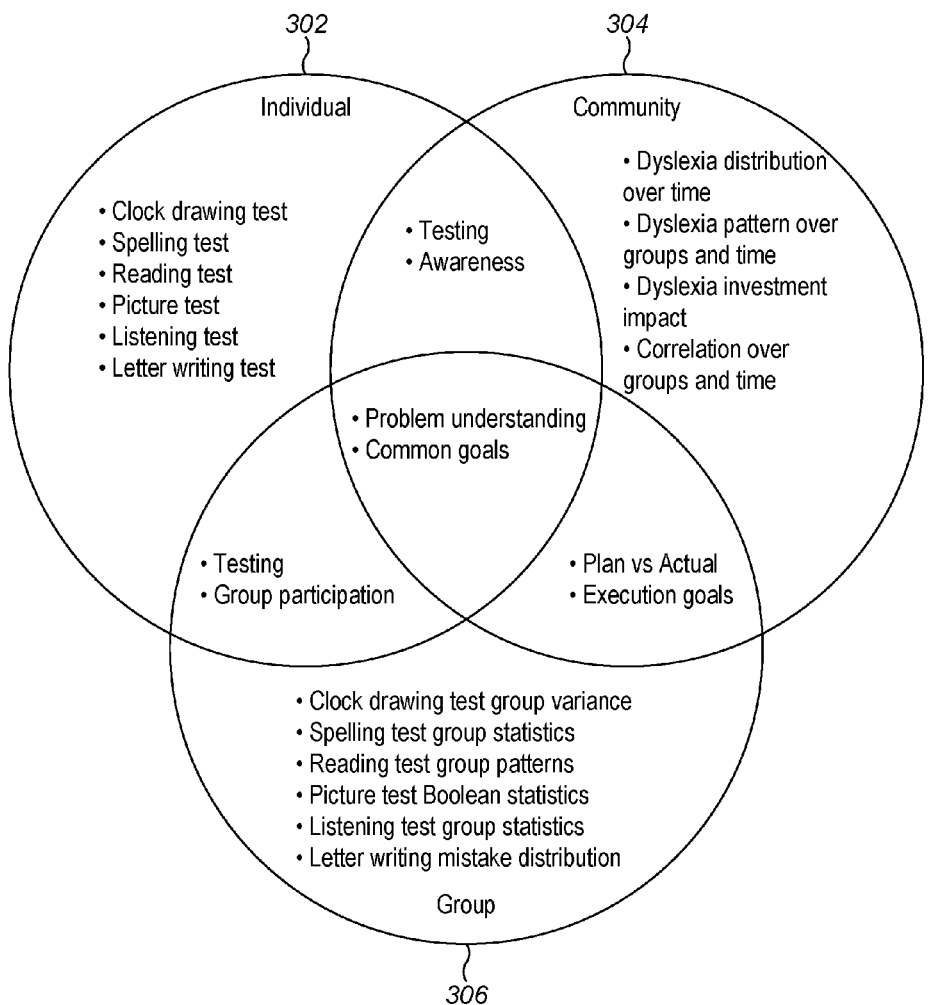
FIG. 3 illustrates the performance metric impacts of the dyslexia testing intelligent system.

FIG. 3 shows the high level performance metric impacts for a user as an individual 302, team or group 306 and community 304 at large and finally the country. The proposed Dyslexia analytics system/Dyslexia management system operates on the individual 302 performance of Dyslexia test tracking metrics such as clock drawing test, spelling test, reading test, picture test, listening test and letter writing test.

FIG. 3 also shows the analysis at the group 306 level, where the group metrics to measure variance, statistics, group patterns and mistake distribution. The productivity measurements affect individuals 302 as their performance constitutes group impact. Hence tracking test results at individual level, holistically leads to group statistics.

FIG. 3 also illustrates the community level analysis, where metrics such as dyslexia distribution over time period, group patterns, investment impacts and correlation over various group at various time and time management that can be tracked. In addition, metrics compared to other communities can provide improvement areas such as screening efficacy, compensation, investment and impact.

Figure 4:
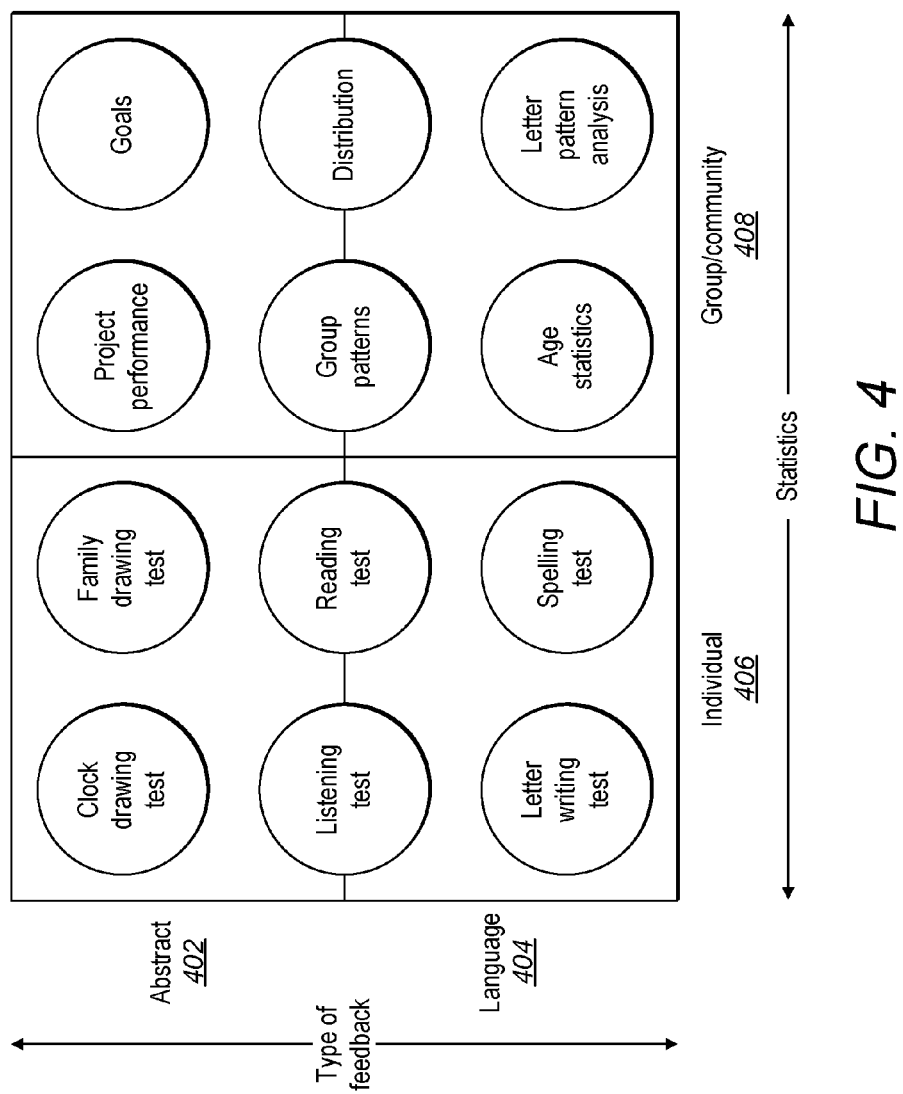
FIG. 4 provides insights into various feedback types.

FIG. 4 illustrates an embodiment where feedback is taken real time in a deterministic and stochastic random fashion. In another embodiment, feedback is taken non-real-time in a deterministic and random fashion, when the test is completed.

FIG. 4 illustrates the different feedback types and the impact it has depending on who the feedback represents. Feedbacks are of two types, Language 404 and Abstract 402. Language 404 test feedbacks are taken through online user interface where tests concentrate on the reading, writing, drawing and spelling aspects. The individual user 406 is tested whether the competency to properly interpret and answer the language aspects through letter writing test, spelling test and reading test. The second type of feedback is more of abstract 402 type, where the test concentrates on the user competency to listen, draw and interpret. Here the user takes a test using the online user interface comprising of listening test, family drawing test and clock drawing test.

FIG. 4 also illustrates the statistics pertaining to individual 406 and group or community 408. The performance feedback for group/community 408 is more filtered and distilled across multiple individuals. For example, the collection of individual language 404 tests are represented at group/community level 408 through age statistics, letter pattern analysis results, distribution and group patterns. For more abstract level feedbacks of group/community 408 are obtained through filtered representation of results at test performance and goal tracking.

Figure 5:
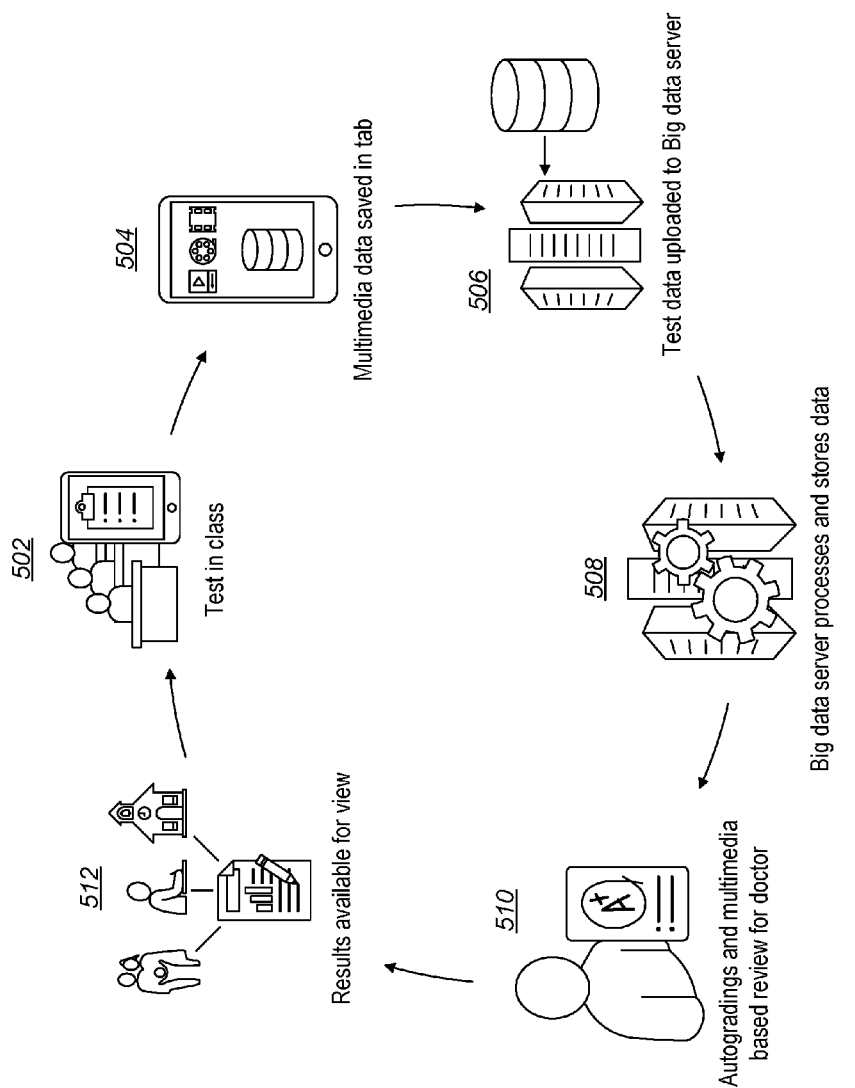
FIG. 5 illustrates the multimedia data flow that occurs as part of the dyslexia screening system operation.

FIG. 5 illustrates the multimedia data flow. From the individual's 406 perspective, the dyslexia test in class is taken online 502. In one embodiment, FIG. 5 illustrates users to use a hand held smart phone 504 to take the test. In another embodiment, the user can take a test using laptop, desktop, tablet or any other electronic, physical and mechanical means. The multimedia data is stored in the electronic device before being uploaded to the backend server 506 through the network. The backend intelligence uses the big data analytics engine in the server to store and process the data 508. The data is viewed by an expert using expert client 510. The expert performs an autograding and multimedia based review before updating the results for view 512 over the network. In one embodiment, the results are available for view over electronic medium. In another embodiment, the results are also available to be viewed in a physical (such as paper) or other (such as audio, braille and broadcast) mediums. In another embodiment, the results are made available to a group.

FIG. 5 shows the high-level architecture of the proposed system. In one embodiment, a school wishing to administer the dyslexia test modules among a group of students first obtains the dyslexia test licenses from the big data server and installs necessary software into required number of tablet PCs. After the test is finished, the multimedia files containing each test module within each tablet PC is uploaded to the big data server, which processes each incoming multimedia test session file and makes the processed raw media files and the auto-grading metadata available for a subject matter medical expert to further view and approve. The auto-grading process at the big data server uses state of the art image processing and gaze tracking methods to assist the medical doctor in filtering and flagging each test module that shows symptoms of dyslexia. The final result is made available to the respective stakeholders.

Figure 6:
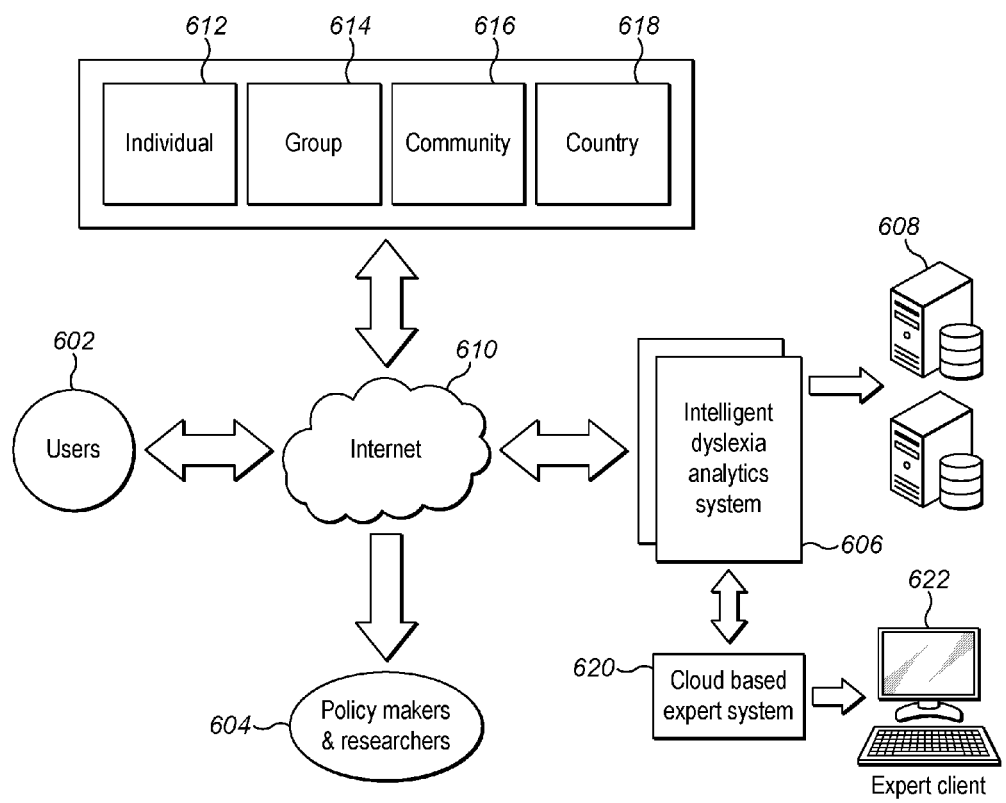
FIG. 6 illustrates the intelligent dyslexia analytics architecture.

FIG. 6 illustrates the intelligent dyslexia analytics system/solution components. The users 602 participate in the dyslexia test online. The users could be an individual 612 or a group 614. The tests are administered locally first and then uploaded to the backend online over Internet 610. The test vectors are captured by the client modules and the test vectors are transferred to intelligent Dyslexia analytics system 606 for analysis. The information is stored in the database system 608. The data is open for expert analysis over cloud based expert system 620 through expert client 622. The results for individual 612, group 614, community 616 and country 618 are used by policy makers and researchers 604.

Figure 7:
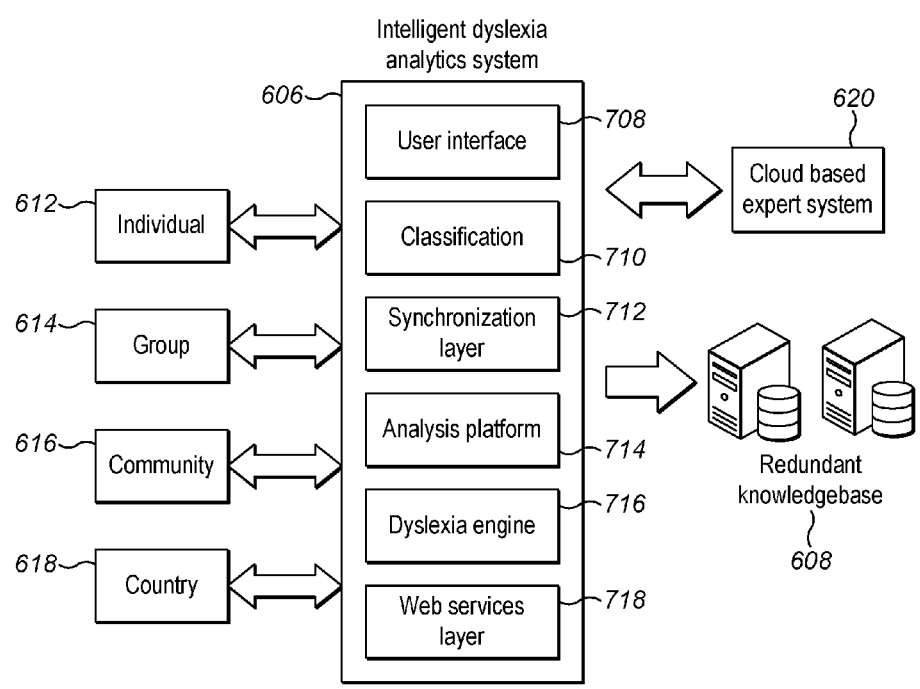
FIG. 7 illustrates the intelligent dyslexia analytics solution and components of the backend intelligence. It also illustrates the dependency on the cloud based expert system.

FIG. 7 illustrates the intelligent dyslexia analytics solution components. The client side test is taken by individuals 612 and the results are compiled for group 614, community 616 and country 618. The client side components directly communicate with Dyslexia analytics system 606 that is intelligent. Dyslexia analytics system 606 has abstraction for user interface 708, classification 710, synchronization layer 712, analysis platform 714, dyslexia engine 716 and web services layer 718. Dyslexia analytics system 606 provides the analytics capability, user interface capability and authentication capability. The backend intelligence interfaces with cloud based expert system 620 through which experts and policy experts access the intelligence system to receive the analytical results for the performance metrics. The Dyslexia analytics system uses redundant knowledgebase 608 to store the data.

Figure 8:
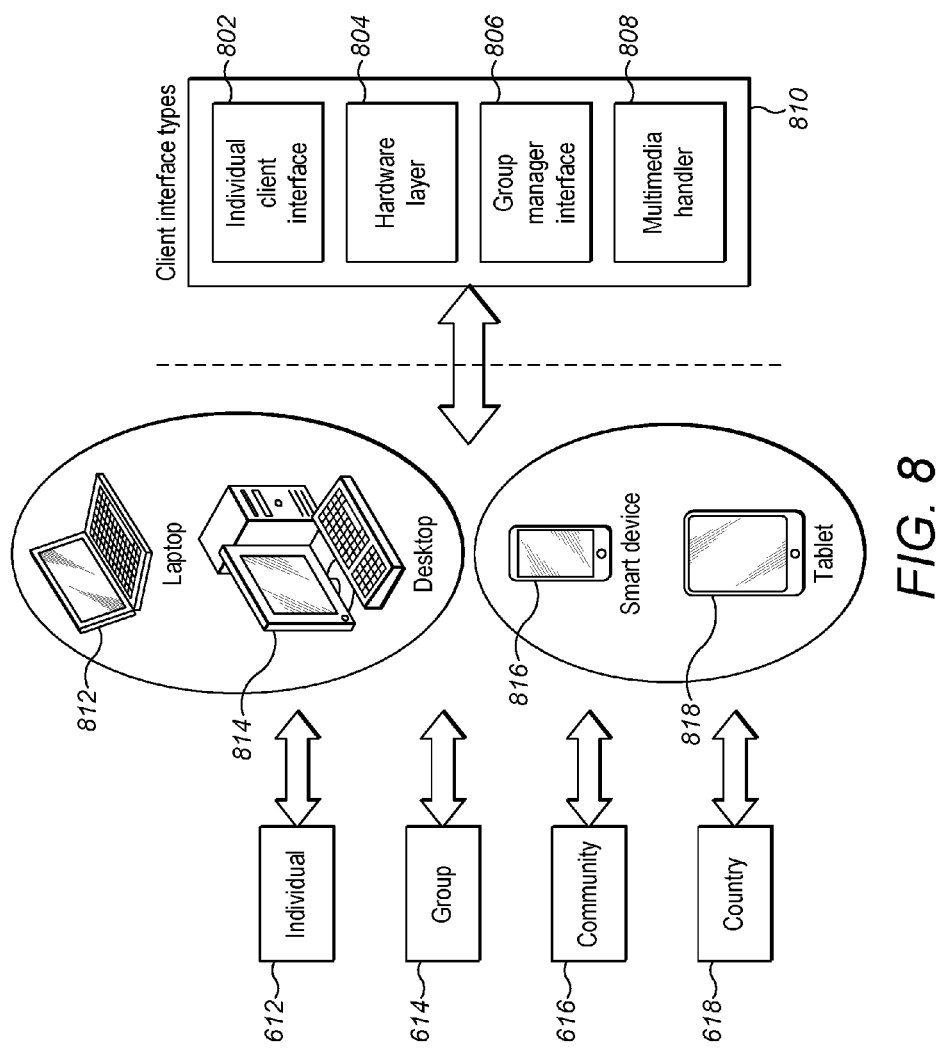
FIG. 8 shows the client side components for the intelligent dyslexia analytics system.

FIG. 8 illustrates the intelligent dyslexia analytics client components. The clients as an individual 612 or group 614 or a community 616 or a country 618 use client components such as laptop 812, desktop 814, smart devices 816 and tablets 818 to perform the test administration. In one embodiment, non-electronic test methods are possible, but needs to be entered into the system manually. The client interfaces, as components within the client devices 810, provide the interfaces to the users 802, hardware layer 804, group managers 806 and the multimedia 808 in backend intelligence system.

Figure 9:
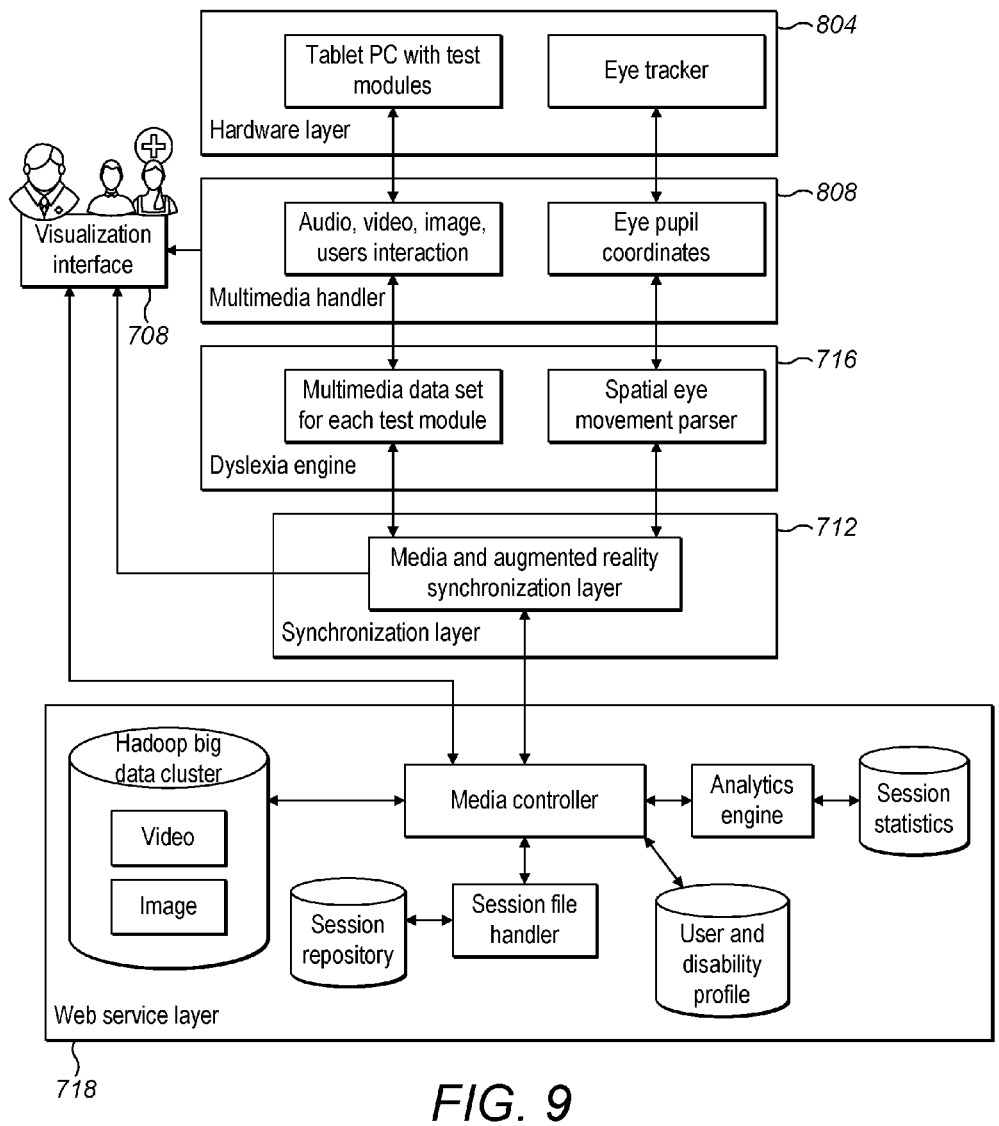
FIG. 9 illustrates the intelligent dyslexia analytics system components.

FIG. 9 illustrates the system components impacted during a testing cycle. The hardware layer 804 in the tablet PC has the test modules and the eye tracker module. In another embodiment, the hardware layer 804 can host the test modules in laptop, desktop and other electronic devices. The test modules provide audio, video and images to the users through multimedia handler 808. The multimedia handlers also provide the eye pupil coordinates through estimation. Both the functions interface directly with the backend intelligence 606 and the visualization interface to the user 708. The audio, video and images are customized per test and obtained from the dyslexia engine 716 in Dyslexia analytics system 606. Special eye movement parser intelligence in dyslexia engine 716 is resident in the backend intelligence 606. Synchronization layer 712 provides the media and augmented reality towards visualization 708. The web services layer provides the total data management 718 interfacing with the Dyslexia analytics system 606. The media controller subsystem provides the intelligence necessary to handle the customized multimedia test modules. The analytics engine provides the number crunching and performance metric estimation and the session file handlers interface with various databases to handle big data analysis. The media controller talks to with visual interface to provide distilled user performance information.

FIG. 9 shows the software components of the proposed system. The Hardware Layer consists of the test environment and the eye tracker sensor. The Multimedia Handler incorporates software library components that handle text, audio, image, and video frames captured during the test time. It also stores user's pupil movement co-ordinates while the user interacts with different test modules. The multimedia is used for capturing rich visual and semantic cues for the doctor analyzer during dyslexia decision making. The Dyslexia analytics system keeps track of individual test modules and stores the multimedia frames per test module in the local memory. It also employs a parser library for the pupil tracker that stores the spatial location of the pupil coordinates with respect to each test module. It attaches test module-based pupil data in the memory. Finally, the multimedia and pupil data are augmented together at the Synchronization Layer to make the final multimedia element as a video file per test module. The video file combines a rich user interaction with the test module elements and eye movement, which is used as a semantic source of the doctor who analyzes the dyslexia pattern. This video is also used at the server side to automatically grade each test module and classify a user as dyslexic or not.

In one embodiment, the Web Services Layer 718 consists of software components that allow receiving any multimedia video test session file, unpacking it, processing different media within the session packet, employing analytics to parse the video files available from different test modules to identify a set of dyslexia identifiers, and finally saving the dyslexia metrics as well as individual media files within relational databases and big data repositories respectively. Media Controller acts as a controller in the MVC Web Services Layer by acting as a proxy between the Synchronization Layer and that of the Visualization Interface. The Media Controller maintains the flow of data at the server side. The user submitted test session file is parsed by the Session File Handler where the raw media (multimedia and pupil movement) is separated and stored in the Hadoop Big Data Cluster whereas the session metadata is stored in the Session Repository. The session metadata is sent to the Analytics Engine, which performs various analyses on the video and pupil data and stores the results in the Session Statistics. User and Disability Profile stores user profile, types of dyslexia patterns observed during a test, types and levels of exam difficulty assigned by the doctor, etc.

Figure 10:
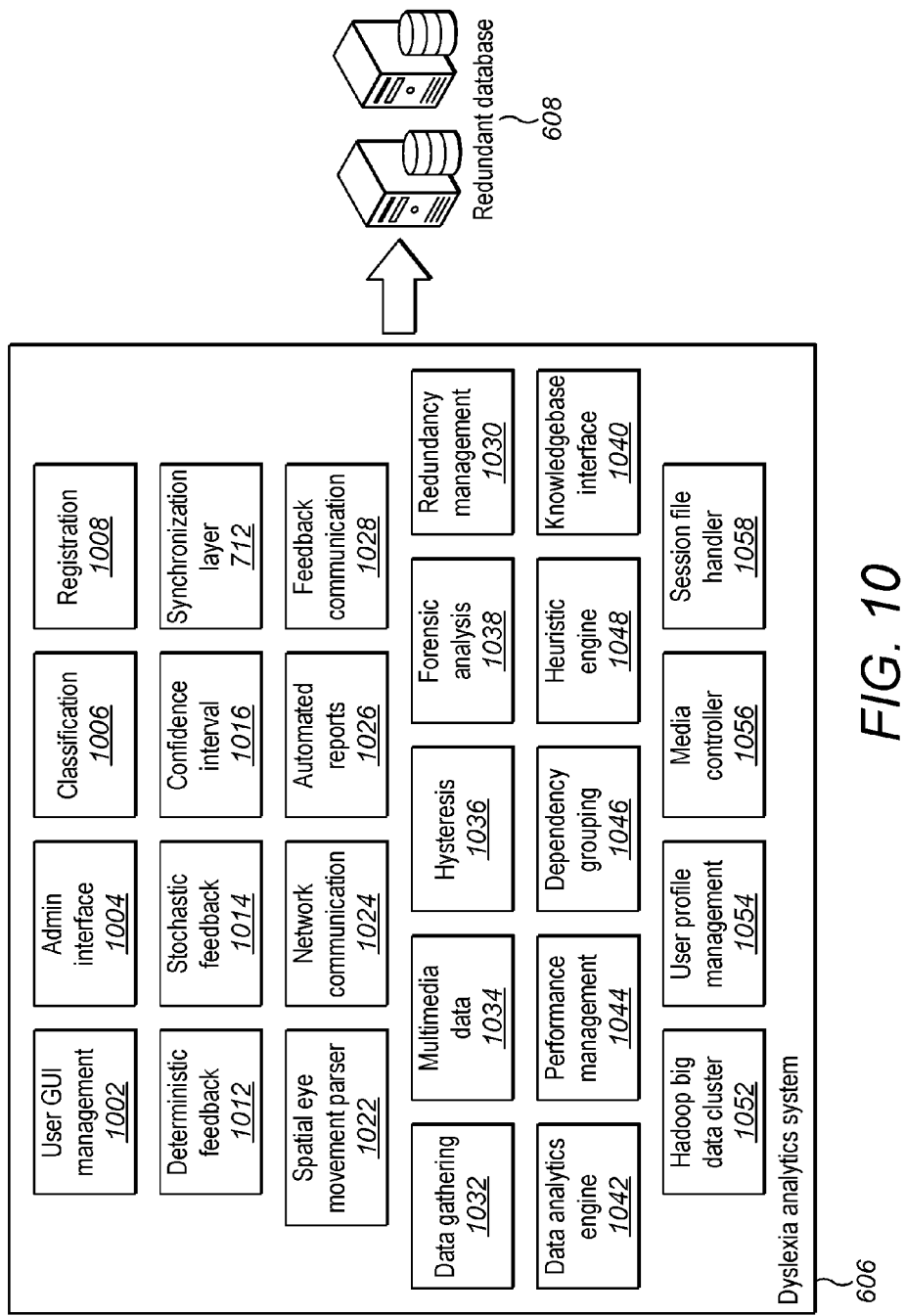
FIG. 10 shows the intelligent dyslexia analytics system server components.

FIG. 10 illustrates the intelligent dyslexia analytics system server components of the Dyslexia analytics system 606. In one embodiment, the user management is provided through Graphical User Interface (GUI) module 1002. The admin interface 1004 provides the high level authentication at user and admin level. It also provides interfaces from where one can buy single or bulk volume test licenses. The classification module 1006 groups the users to various classifications such as school, community and sections. The registration module 1008 provides the registration of users, doctors, experts and policy makers.

FIG. 10 also illustrates the feedback mechanism for various test modules. The feedback analysis is conducted for both deterministic 1012 analysis and stochastic analysis 1014. Confidence interval 1016 for the stochastic analysis is performed for accuracy of the statistical analysis. Spatial eye movement parser 1022 provides the dyslexia engine the capability to monitor the eye movement and analyze. Network communication module 1024 handles the backend server connectivity. Automated reports 1026 generates reports for experts, doctors and policy experts in specified formats. Feedback communication 1028 module interfaces with multimedia handlers to display through visual interface to the end user. Data gathering 1032 module interfaces with client devices to get the test data. Multimedia data module 1034 interfaces with multimedia handler 1056. Hysteresis 1036 module handles the analysis of the data over various users in group and over various time intervals for drawing intelligent conclusions. Forensic analysis 1038 module provides the function to analyze data that have been in the past to understand the trend in a particular group or community. Redundancy management module 1030 provides the interface to manage the redundant database 608. Data analytics engine 1042 the brain module to analyze the data using the web services layer 718 components such as Hadoop big data cluster 1052, session file handler 1058, knowledge base 1040 and heuristic engine 1048. The data analytics 1042 provides trends, performance graphs and other useful data for drawing proper conclusions towards policies and goals. The performance metrics are managed through performance management 1044. The individual and users are grouped into logical equivalence classes using dependency grouping 1046 to track the dyslexia impact within a group. The group profiles are managed for security using user profile management 1054.

Figure 11:
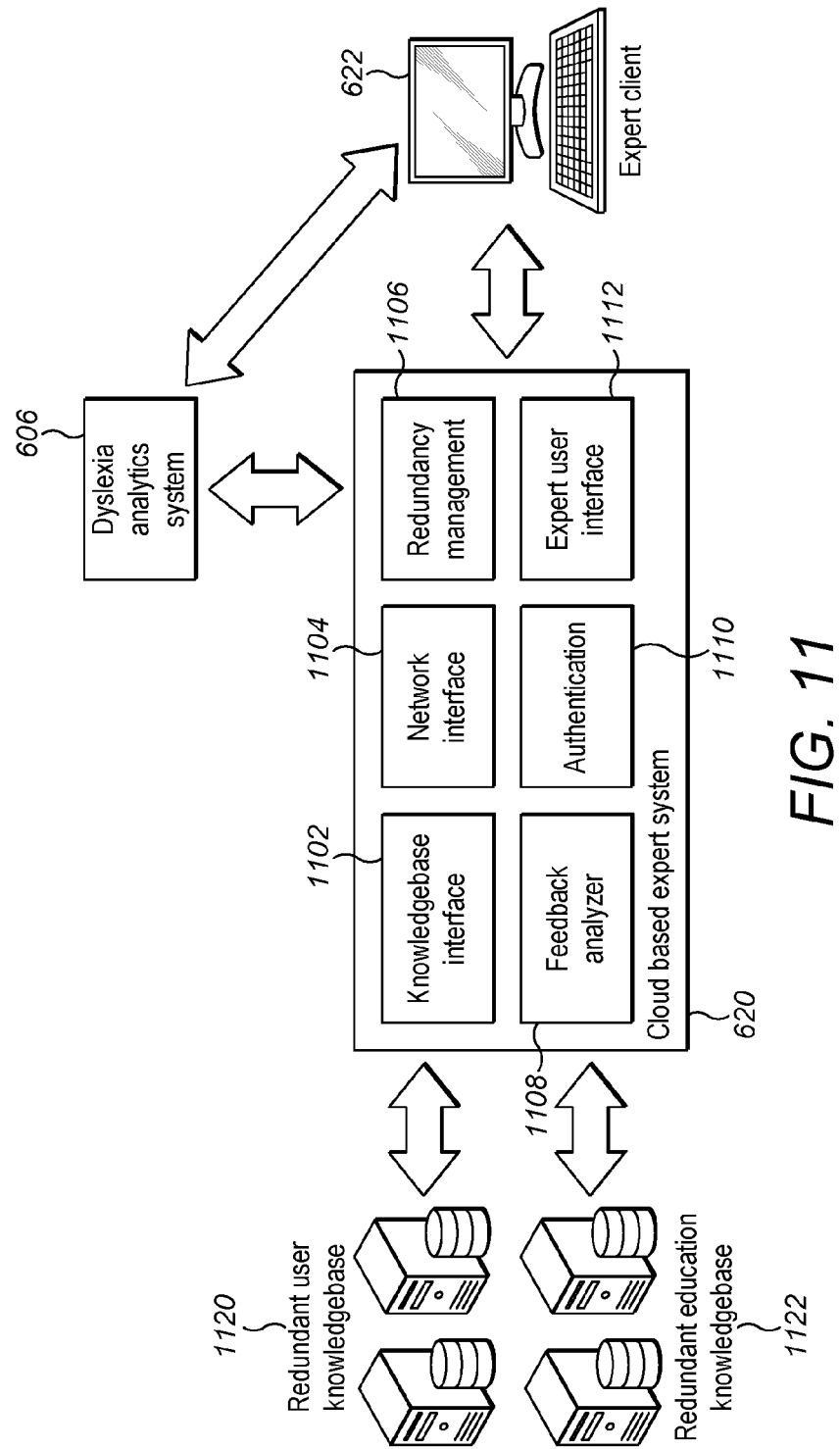
FIG. 11 illustrates the cloud based expert system components and the dependencies to the backend intelligence. The figure shows the expert client interface and the interfaces to the redundant knowledgebase.

FIG. 11 illustrates the expert system architecture. The cloud based expert system 620 provides the important function for experts and analysts to further research and analyze the data collected by Dyslexia analytics system 606 and use the data analytics obtained through the Dyslexia analytics system 606 to draw important macro level conclusions. The expert system 620 interfaces with expert system user knowledgebase 1120 which contains important user level information. It also interfaces with the redundant education knowledgebase 1122 that consists of the learning due to dyslexia patters within groups and communities for training doctors, experts, social workers, and other health care workers. The expert system 620 consists of knowledgebase interface 1102, network interface 104, redundancy management 1106, feedback analyzer 1108 and authentication 1110. The expert clients 622 login through network 1104 and the expert user interface 1112 and are authenticated 1110 before accessing the feedback 1108 using redundant knowledgebase 1120 and 1122. The redundancy and fault tolerance of the knowledgebase 1120 and 1122 is handled through redundancy management 1106.

Figure 12:
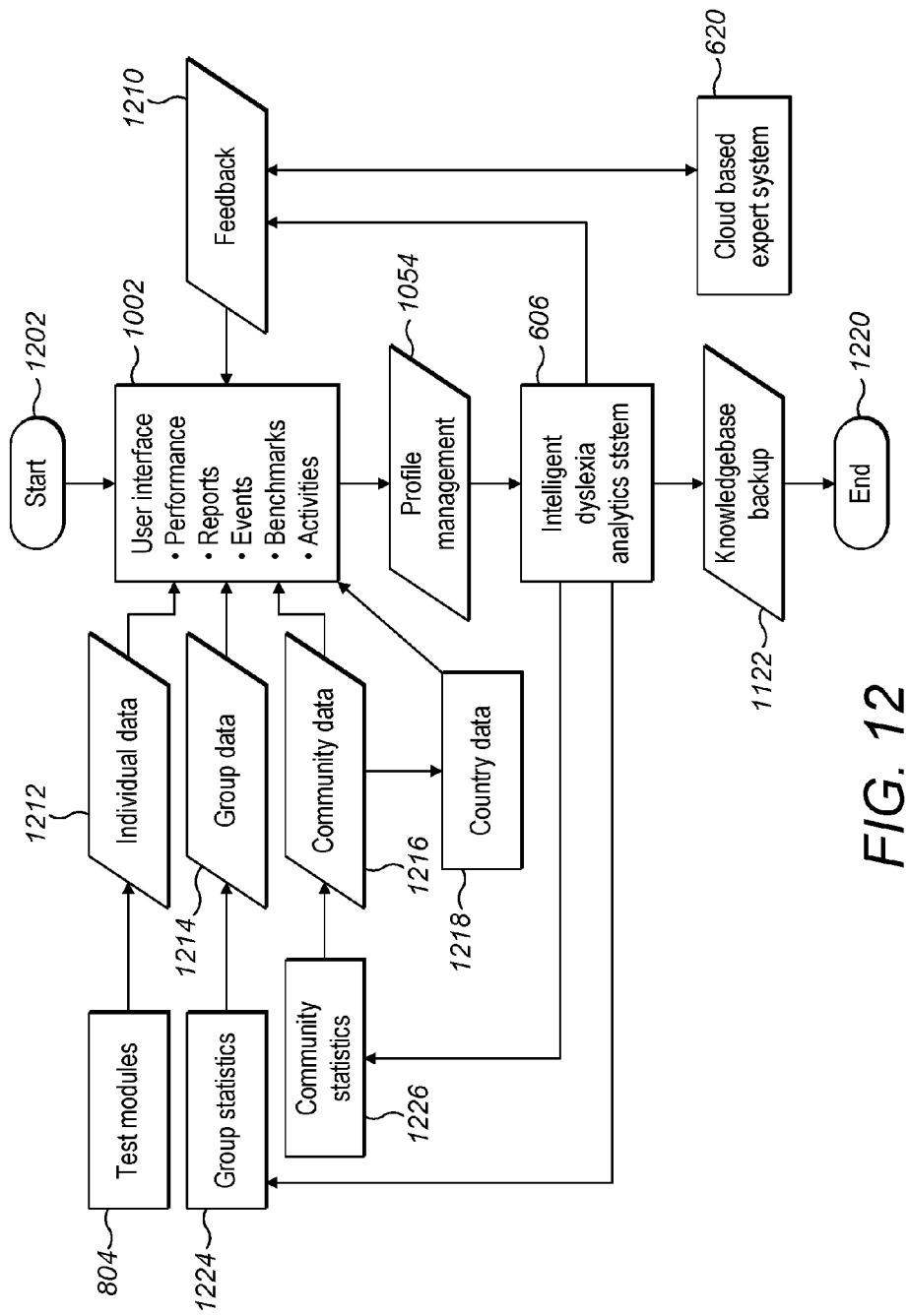
FIG. 12 illustrates the control and the data flow to the user interface for user and doctors.

FIG. 12 illustrates the control and data flow to user interface 1002. The visual interface 708 for individual users and groups captures performance, reports, events, benchmarks and activities. The data is fed as individual data 1212, group data 1214 and community data 1216. The individual data 1212 is received through test modules 804 from user interfaces in client device components. The group data 1214 and community data 1216 are received through group statistics 1224 and community statistics 1226 received from the backend intelligent dyslexia analytics 1042. The user interface data is provided based on profiles 1054. The data are stored in knowledgebase 1120 and 1122. The user interface also collects data through expert system 620 analyses and the feedback based on the analysis 1210.

Figure 13:
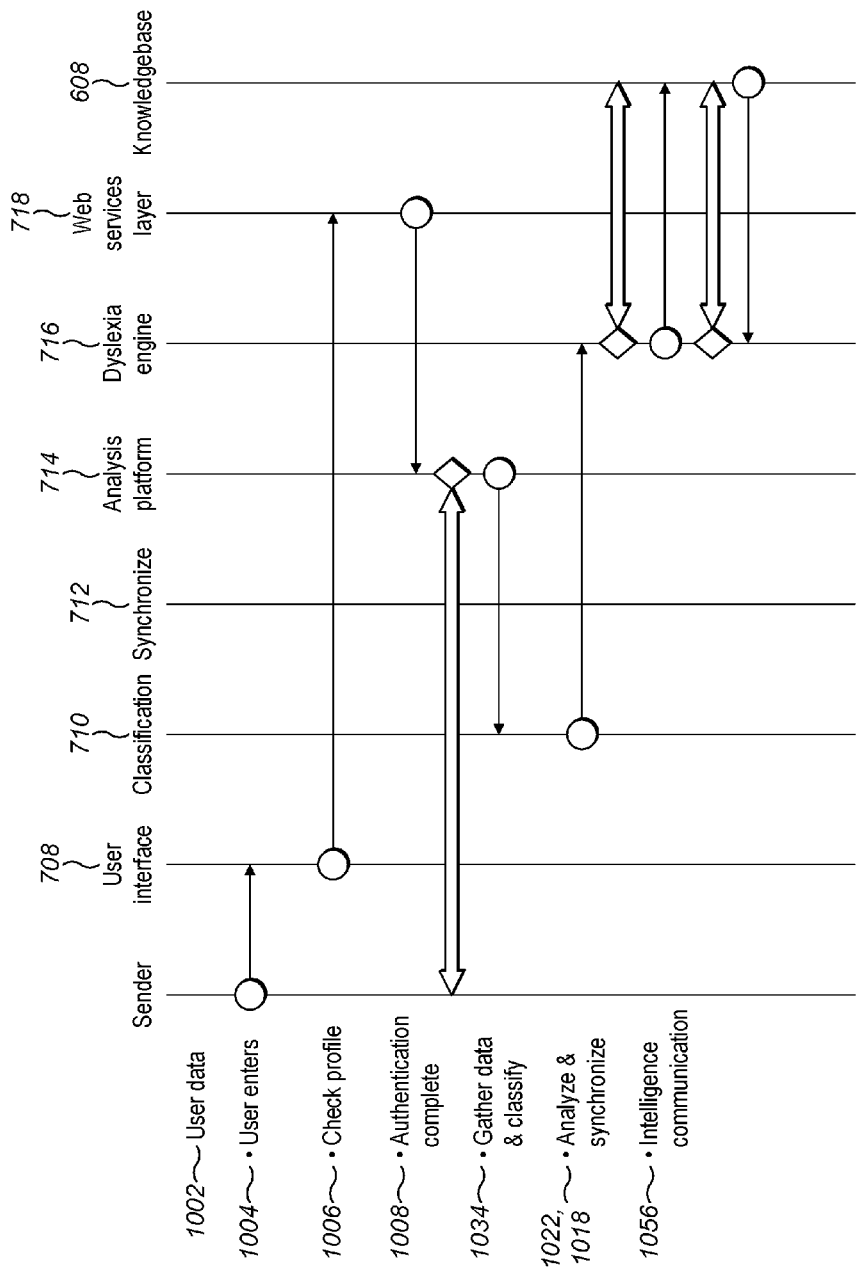
FIG. 13 shows the high level message sequence diagram illustrating a user using the system.

FIG. 13 illustrates the message sequence chart for user data flow 1002 as part of feedback gathering and analysis. User enters the login certificates 1004 and the user interface 708 authenticates and the profile is checked 1006. The web services layer 718 receives the data and the authentication process is completed 1008. The end user starts inputting the dyslexia test data, which are gathered 1034 and sent to dyslexia backend engine 716, for analysis 1022 and synchronization 1018. The data is stored in knowledgebase 608. The analytics metrics derived is communicated back 1056 to visual interface.

Figure 14:
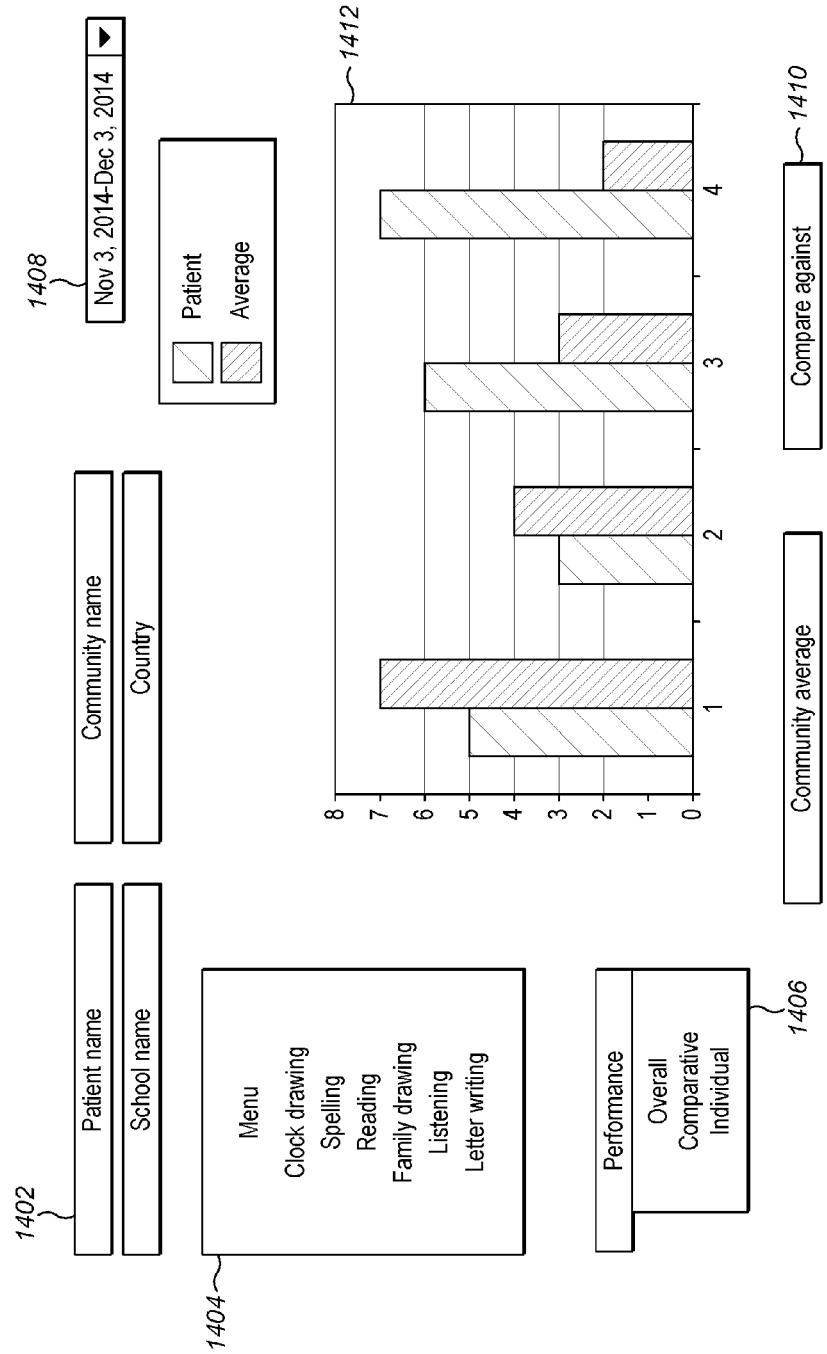
FIG. 14 illustrates one example display generated by the user interface allowing a user or an expert such as doctor to view the results. The results are displayed at various granularities.

FIG. 14 illustrates an embodiment of user interface screen. The granularity of the data 1402 is at patient, school, community or country level. Time period of the analysis is entered 1408 for analytics. The comparison can be done between patient/user and the average group 1412 as graph. The menu can be used 1404 to specify the metric that needs to be compared. The performance 1406 can be either for overall country level, group level or individual level for mean analysis.

Figure 15:
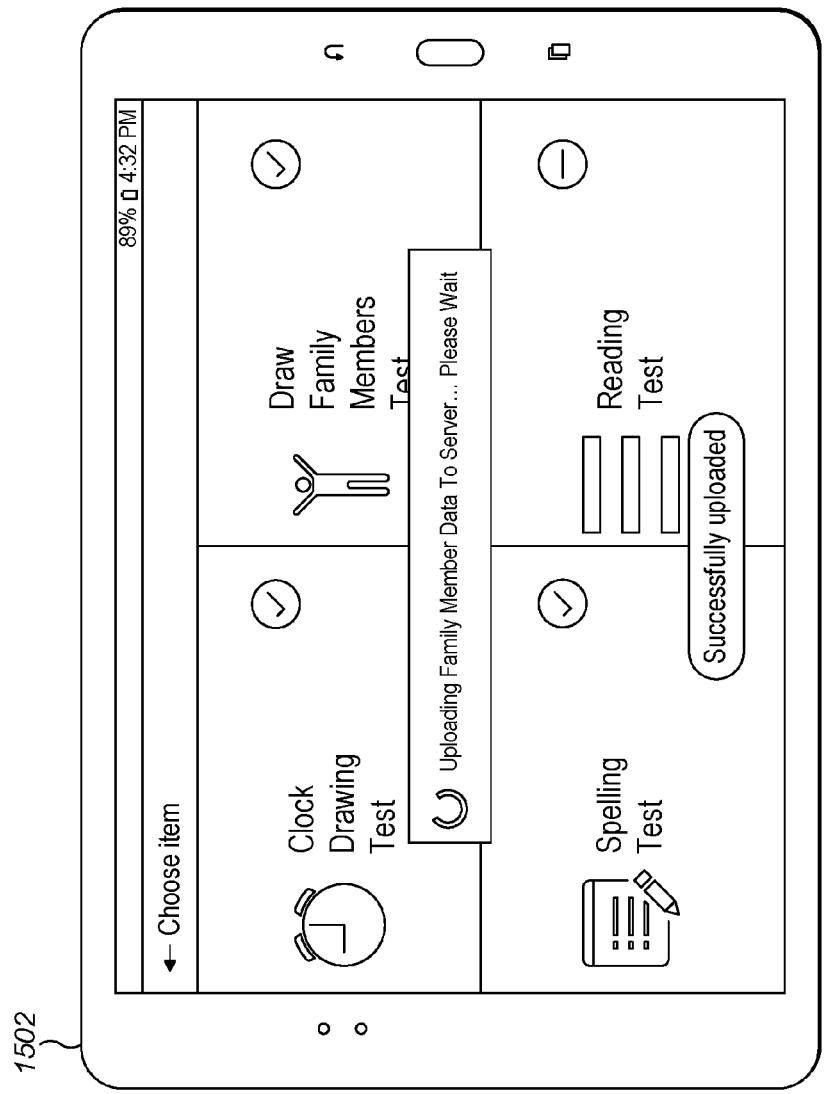
FIG. 15 shows an embodiment of example inputs into the dyslexia system application, and tests for the user.

FIG. 15 illustrates the dyslexia test types using tablet 1502. In another embodiment, the four tests can be conducted using any electronic device with a touch screen and camera attached or built-in for gaze/pupil tracking.

Figure 16A:
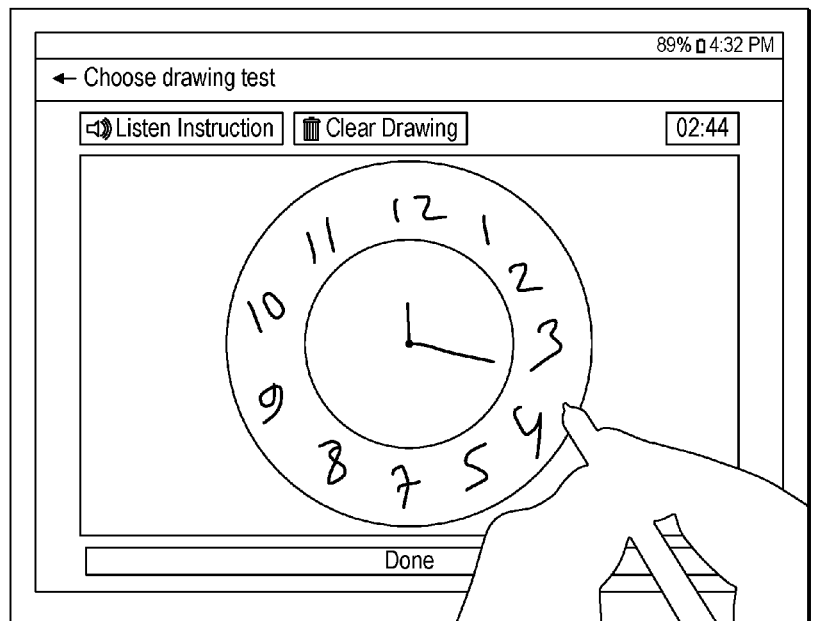
FIGS. 16A and 16B shows an embodiment of example of the clock drawing test.
Figure 16B:
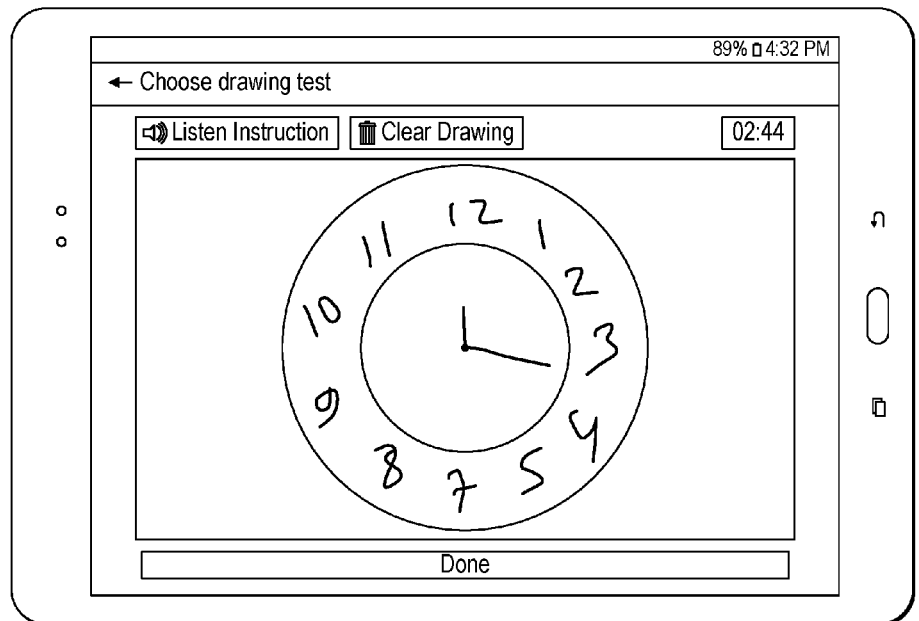

FIG. 16A illustrates the clock drawing test using tablet 1602. In FIG. 16B the data is captured using stylus 1604 in a proper figure pattern as done by the end user for accurate depiction. This test presents an empty circle and a button to press to give a subject a verbal instruction to fill in the clock to show e.g. 12: 20 am. While a user performs the test, methodology tracks the drawing anomaly and allocates marks for different strokes. Different kinds of anomaly patterns are described in the doctor assessment module.

Figure 17A:
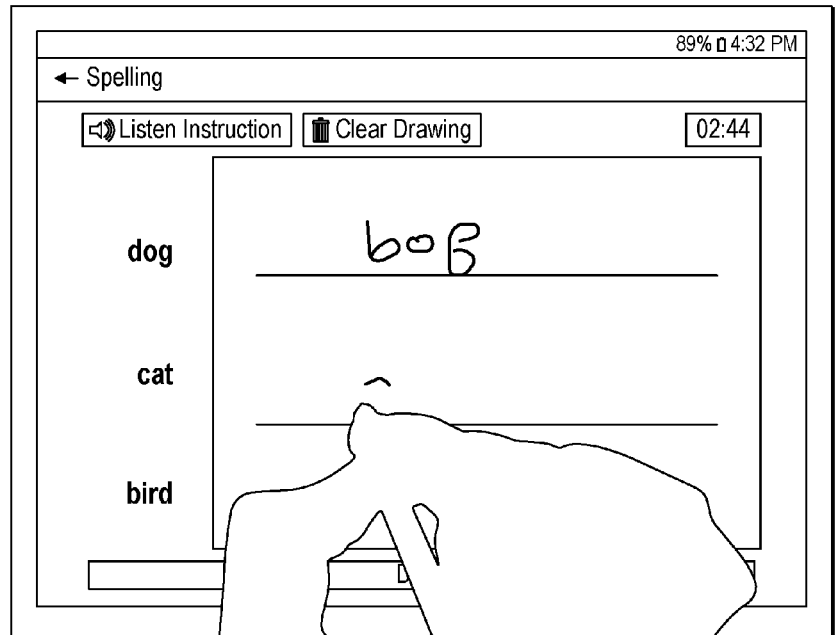
FIGS. 17A and 17B shows an embodiment of example of the writing test.
Figure 17B:
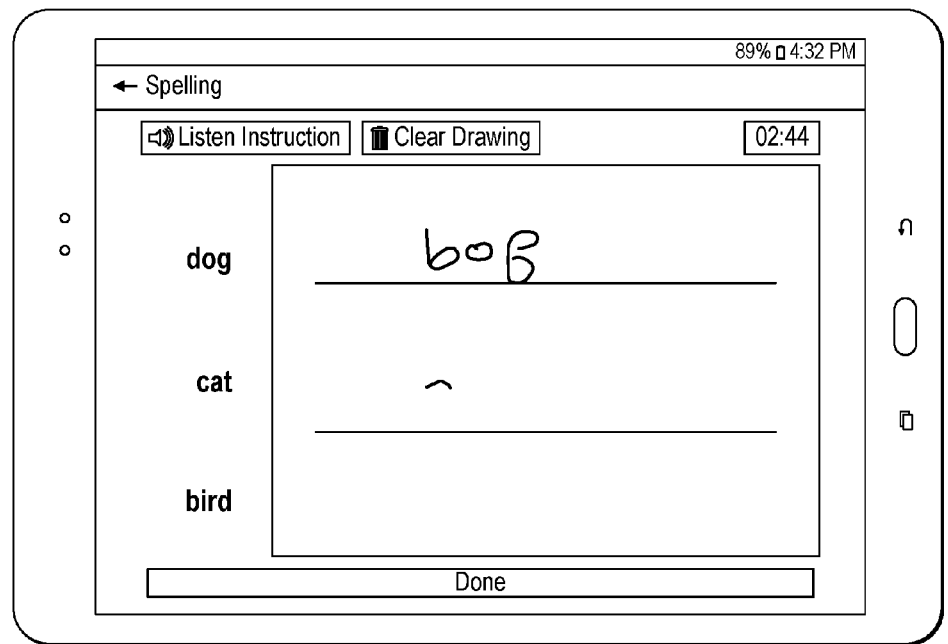

FIG. 17A illustrates the writing test, where the user uses stylus to write 1702 the answer. The answer in terms of incremental stroke images is captured by the device 1704 for further analysis as shown in FIG. 17B. A number of writing anomalies are detected through this module. For instance, there is a word cat and numbers 69345. For each section, the methods look for reversed and missing letters. Since the way they are written are stored as multimedia screencast videos, the examiner can see how the letters e.g. e, a, p and b are written. By retracing the video of the test as it is written to see where the start and end is, a judgment about sloppy, missing, reversed, and uneven writing can also be made.

Figure 18A:
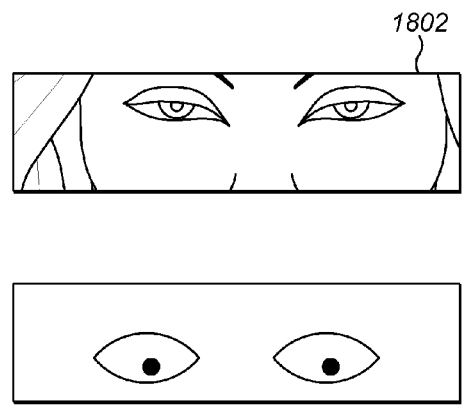
FIGS. 18A and 18B illustrate an example of the reading test.
Figure 18B:
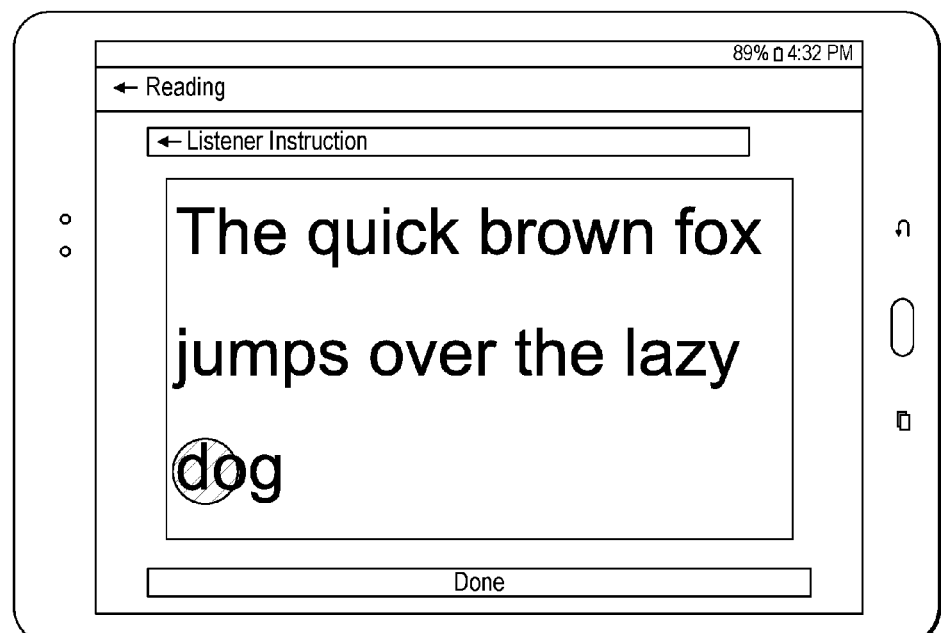

FIG. 18A illustrates the reading test, where the eye movement is monitored using camera 1802. Number 1806 specifically shows the position of the pupil while taking the test. The data of eye movement concentration area within the sentence is captured 1804 for further analysis in FIG. 18B. Dyslexics tend to show unorganized vertical or horizontal or circular eye movements. This test indicates abnormal eye movement and the examiner can go back and listen to the recorded speech and also see the eye movements recorded as video while hearing it to see if the candidate could follow the written materials. The FIG. 1802 shows how the eye coordinates are superimposed on top of the text while it is read and finally sent to the server side for the doctor analyzer to observe.

Figure 19:
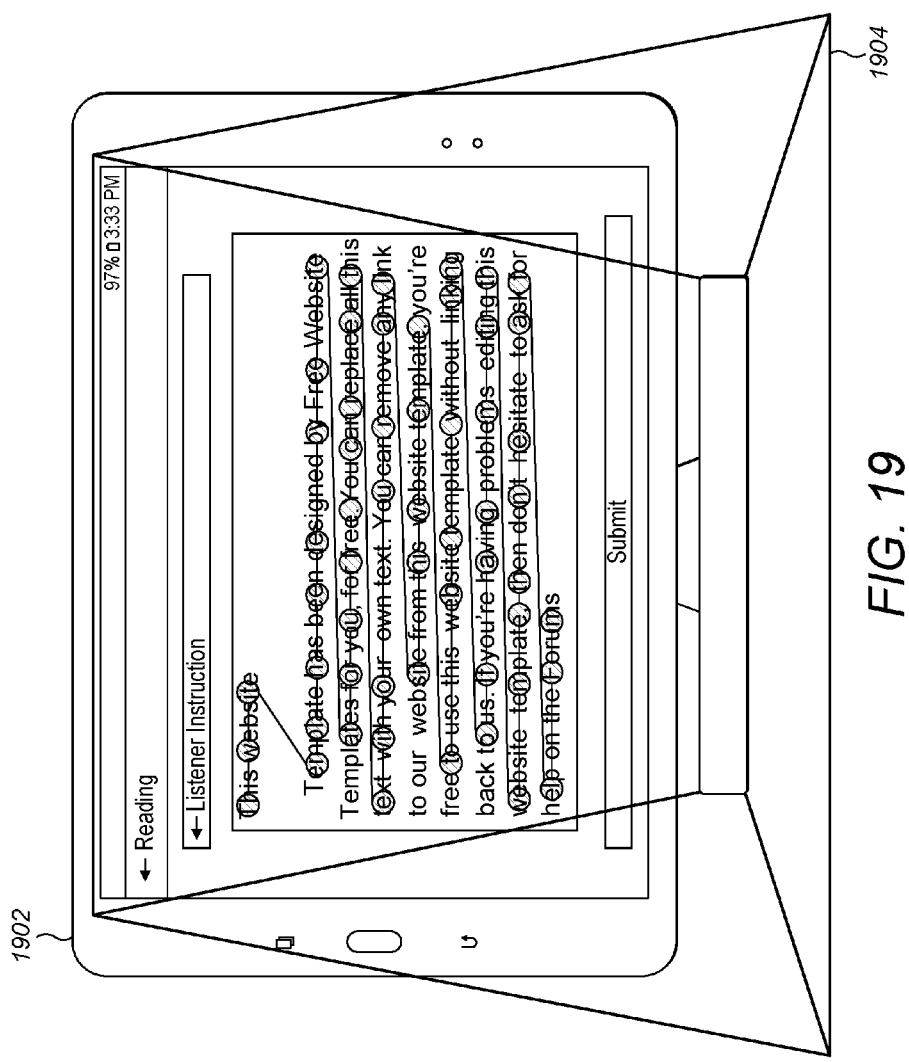
FIG. 19 illustrates the pupil movement tracking.

FIG. 19 illustrates the pupil movement tracking for the complete paragraph in the tablet 1902. The pupil movement captured through camera is highlighted in the screen 1904 for further analysis. The projected shared area 1904 in front of the monitor or screen shows the field of view of the camera in which the best pupil recognition takes place.

Figure 20A:
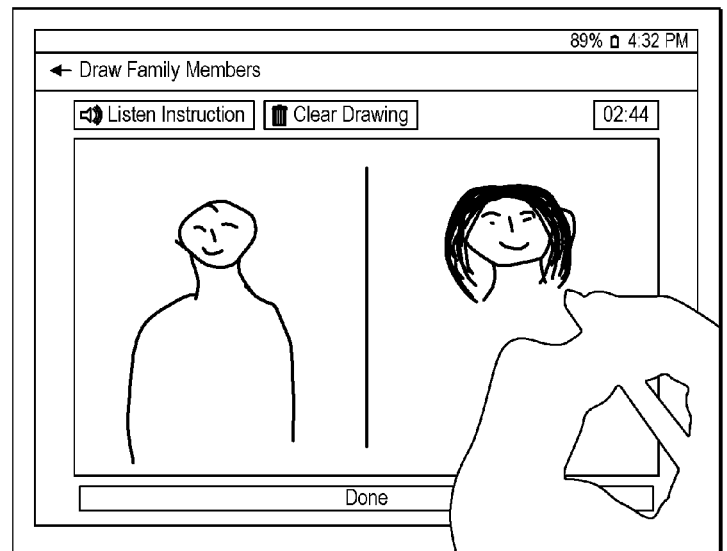
FIGS. 20A and 20B shows an example of the family member drawing test.
Figure 20B:
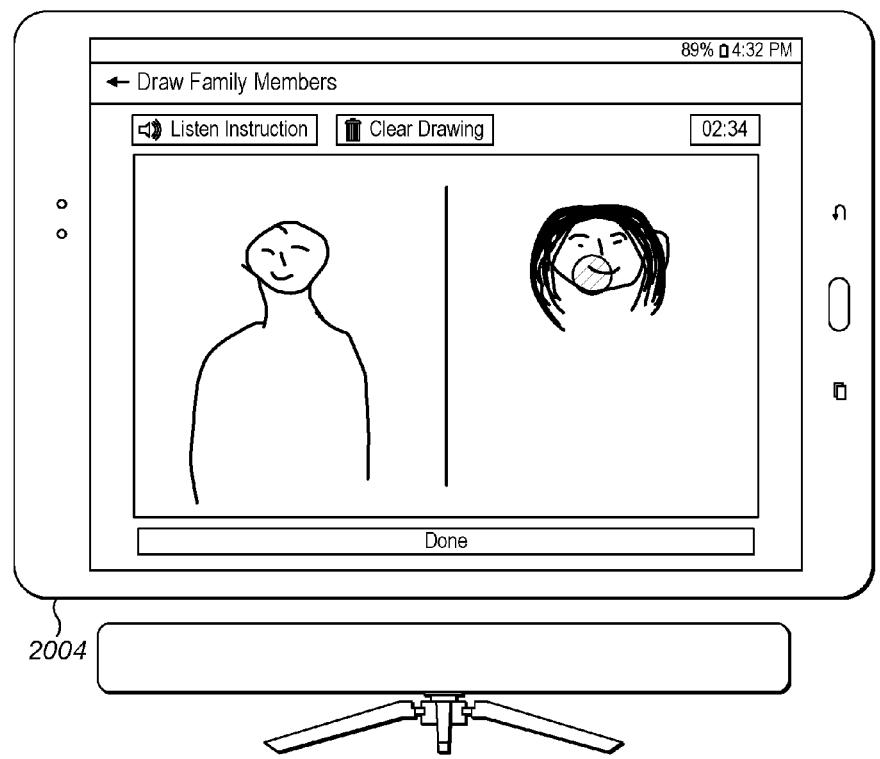

FIG. 20A illustrates the drawing family members test, where the stylus is used by the user to capture the illustration of the family member 2002. In FIG. 20B the user interaction data on the screen is captured as images by the device for further analysis 2004 at the Dyslexia analytics system 606 is shown. A subject will be asked to draw two family members e.g. father and mother. The way the subject draws the family members is tracked and the method identifies whether there is dyslexic pattern observed. The pupil movement data is also saved as multimedia for assisting the doctor analyzer. Different kinds of granularity of the drawn objects are observed by an auto-grading method. For example, how many features are drawn by a student: is it just a bare skeleton, or have hairs, nails, dressed up, all fingers, eye brow, flesh, and complete number of salient body part.

Figure 21A:
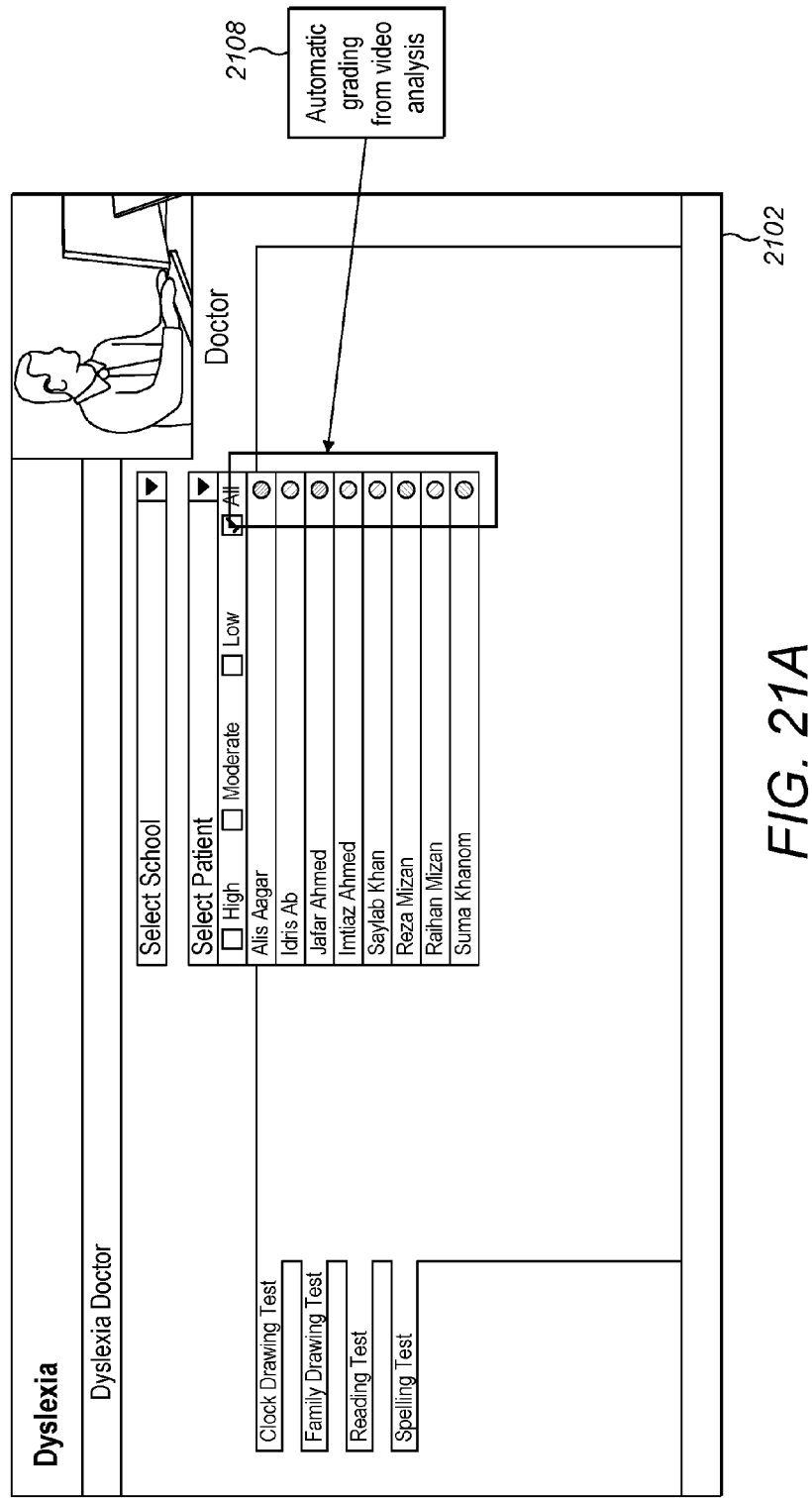
FIGS. 21A, 21B, 21C, 21D and 21E shows an example of test data analysis by the cloud based intelligent analytics engine and presented as summary to be viewed by a human experts based on audio, video, text, drawing, and pupil movement data analysis.
Figure 21B:
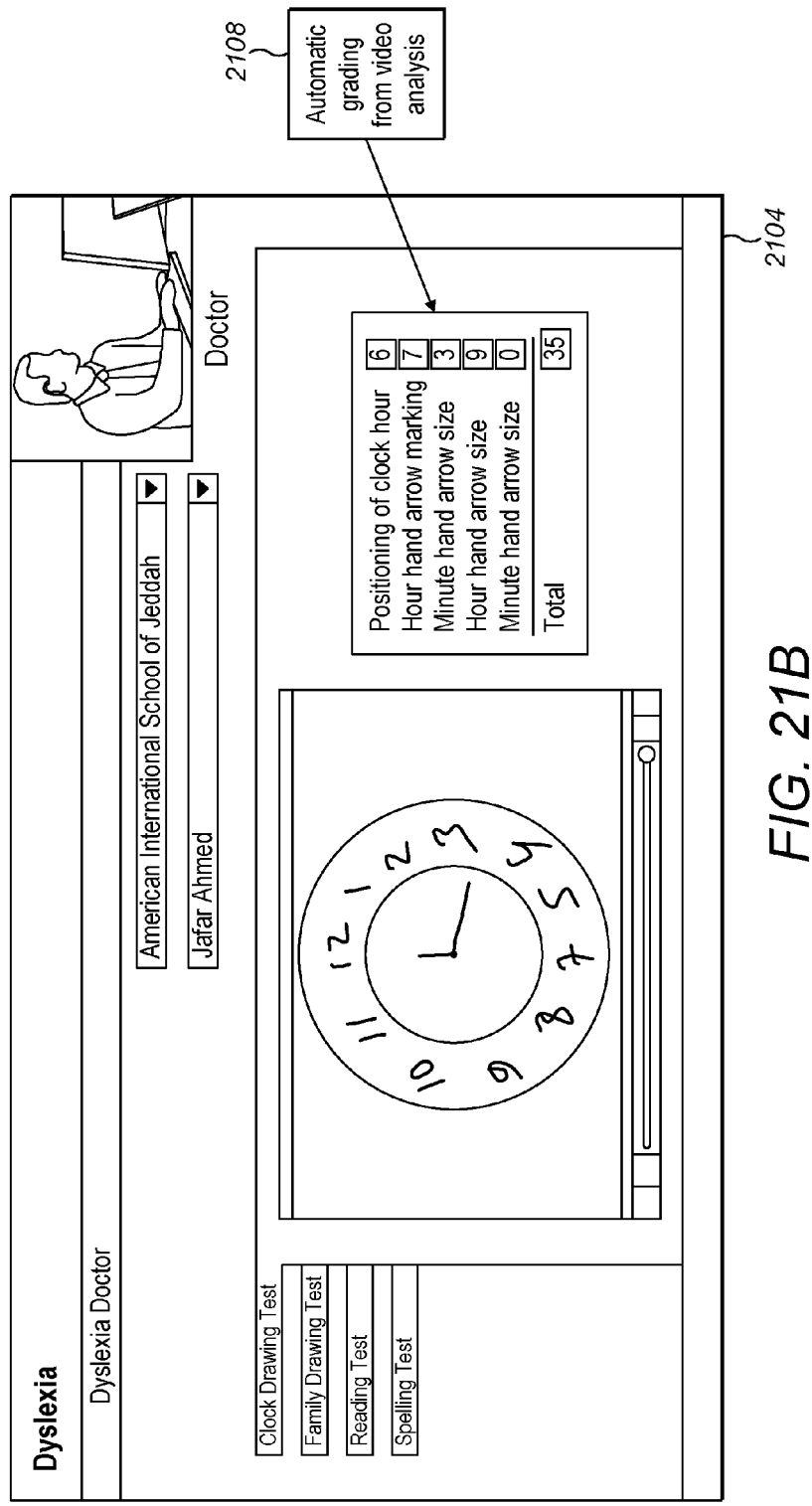
Figure 21C:
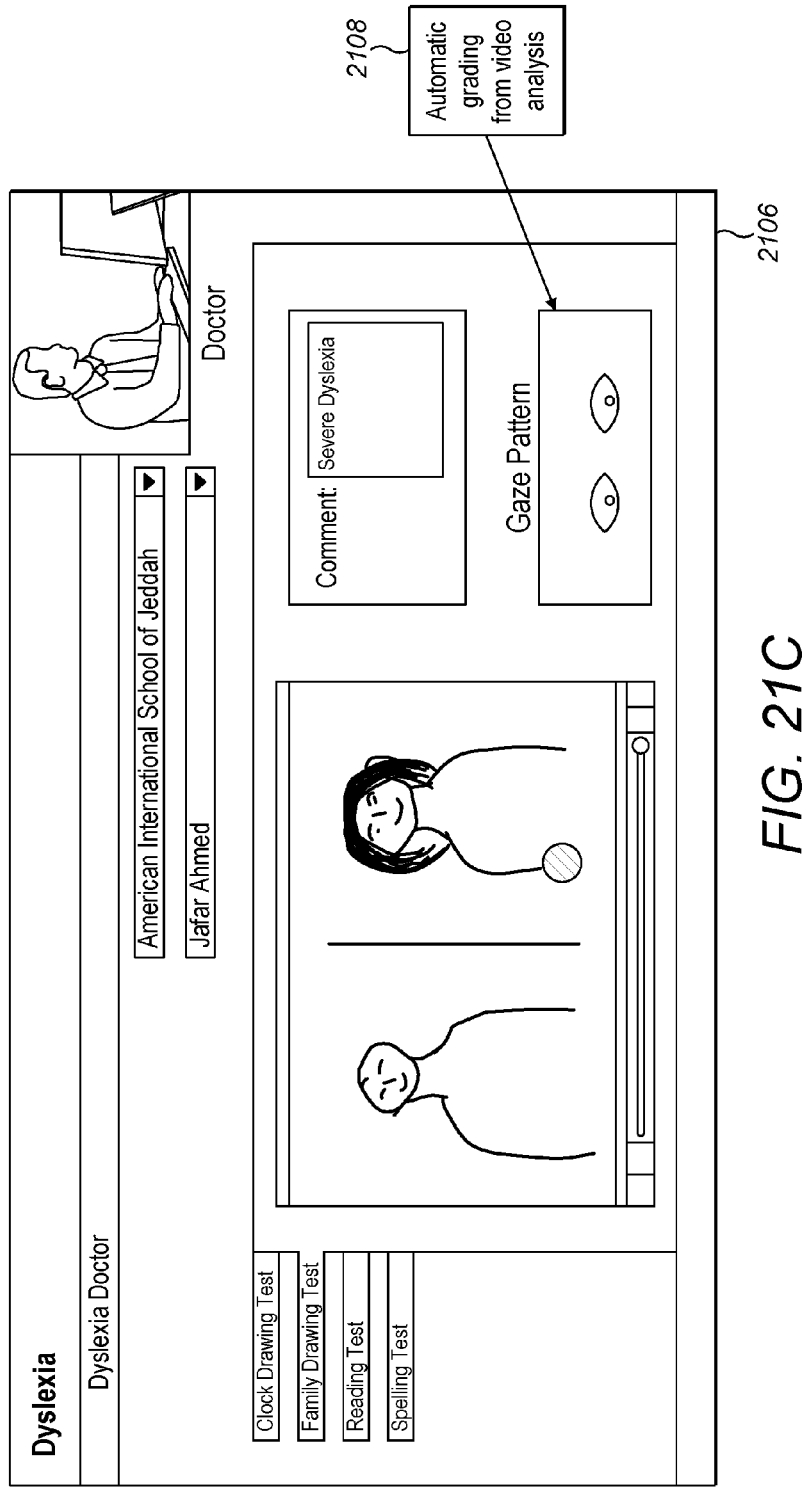
Figure 21D:
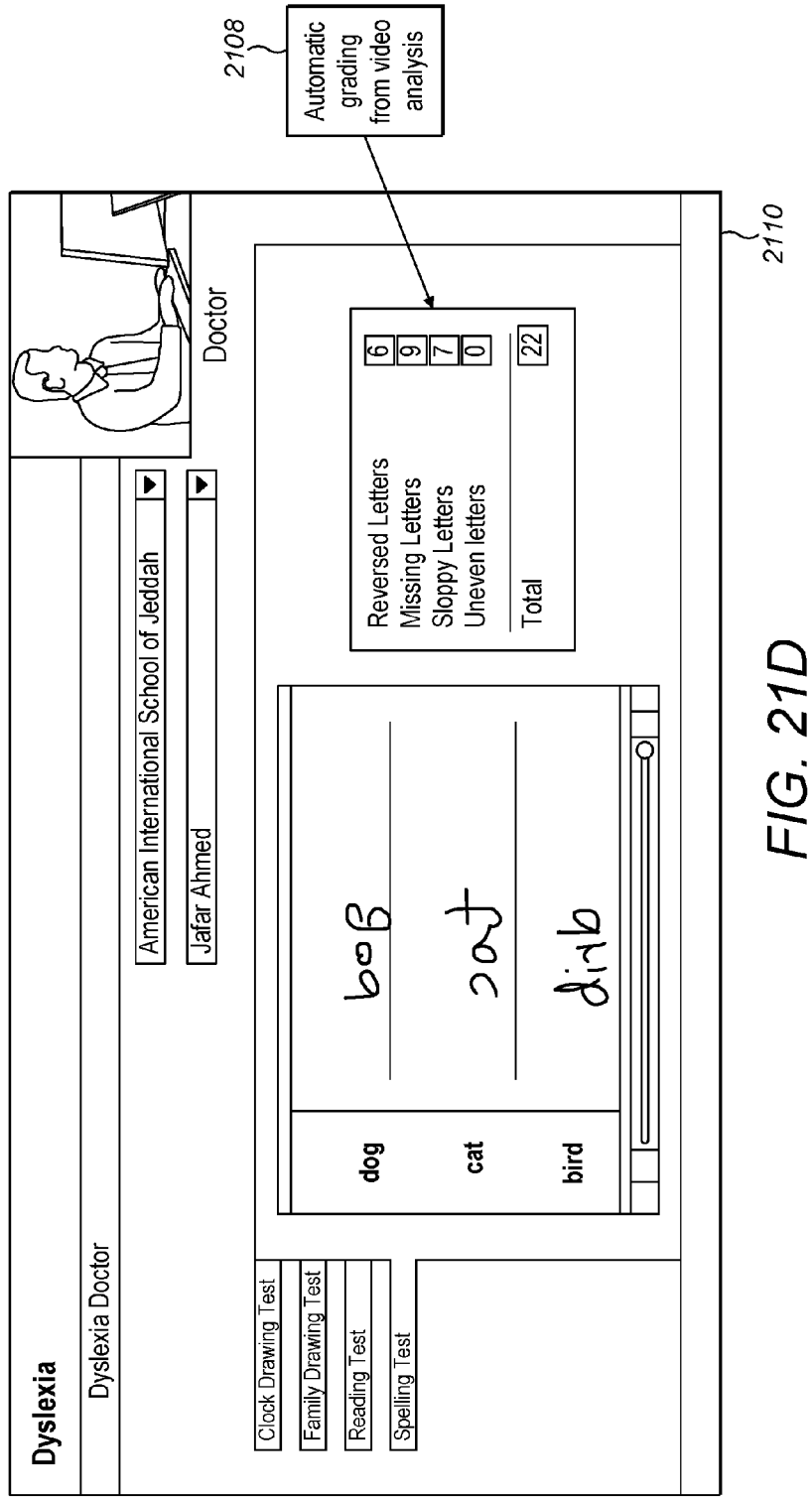
Figure 21E:
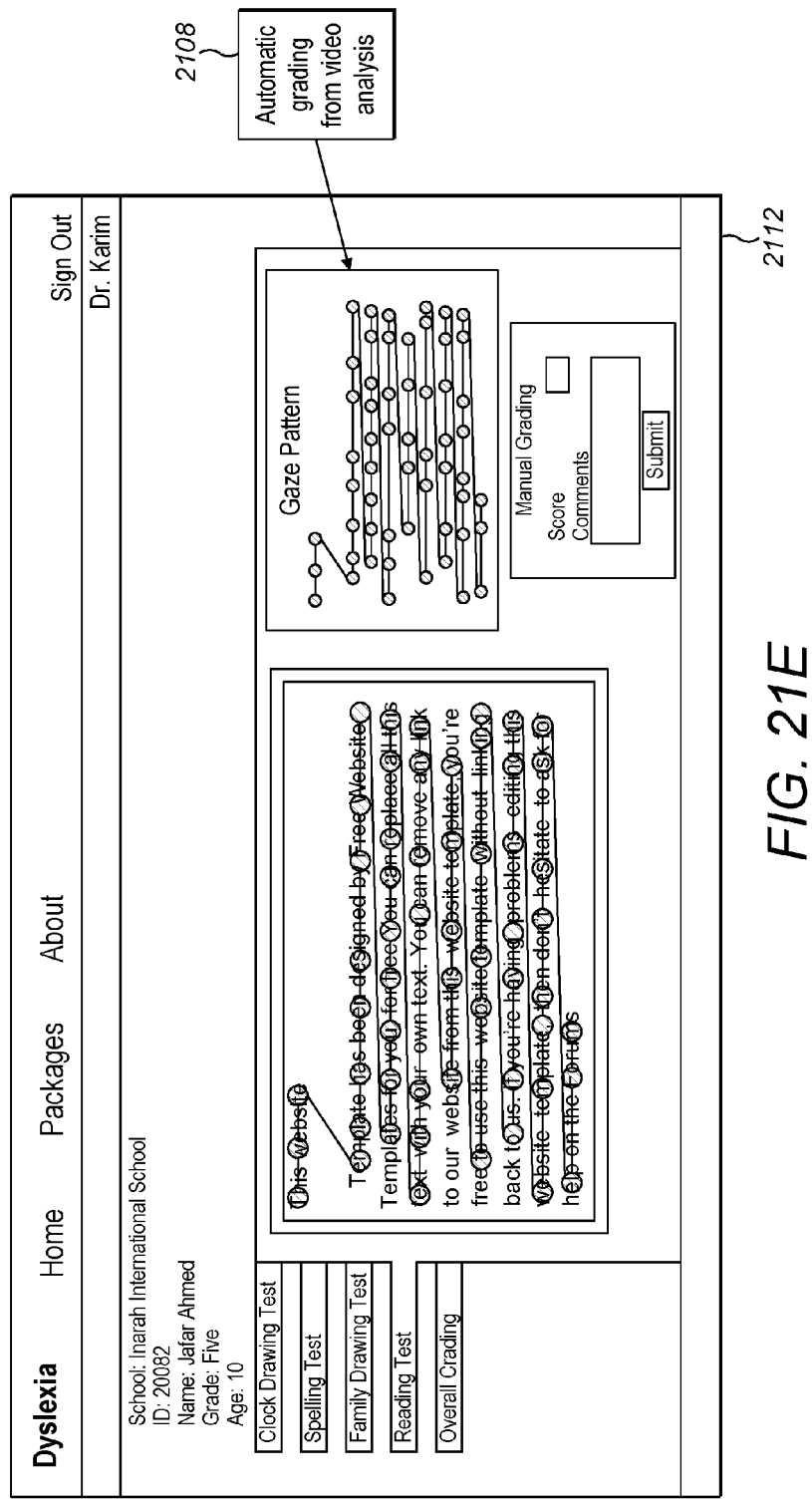

FIG. 21A illustrates the data analysis of the complete user test by an expert using automatic grading from video analysis 2108. The backend intelligence provides the captured data through expert client to view the analytics and the raw data over user interface for making important conclusions. At the end of each test module, the interaction data is captured by saving the screencast video, and audio stream, storing them locally at the tablet, and attaching user profile and session metadata. Once all the test modules are performed within the given time, the multimedia files containing dyslexia patterns can be uploaded to the big data repository. FIG. 21B shows a sample instance where one test module is being uploaded to the server.

FIG. 21 shows the user interfaces of different doctor modules. User interface 2102, shows the result of automatically tagging each student's submitted test results. Different color index shows different tagging e.g. red circle shows a confirmed dyslexia pattern found by the auto-grading method, yellow represents a possibility and hence requires the doctor to confirm it and a green means the test results exhibit no dyslexia patterns. This color scheme is used to assist a doctor with a high level overview of the test results for mass screen. A doctor can always go to any particular or all test results to approve the dyslexia patterns manually. In FIG. 21B user interaction video 2104 and the automatic grading done by server side methods on the basis of positioning of clock hour, hour hand arrow marking, minute hand arrow marking, hour hand arrow size, and minute hand arrow size is shown. The video shows the incremental buildup of the clock, which will give the doctor an idea how the drawing was performed over time as well. In FIG. 21C a Clock drawing test video 2106 synchronized with the spatial eye movement pattern during the test is shown. The eye movement pattern and the formation of different parts of the body give an indication whether the subject is dyslexic. A doctor can mark his/her comments on the observed video and gaze data. In FIG. 21D a Writing test 2110 and the auto marking of the writing, based on the video or image analysis on reverse, missing, sloppy and uneven letters is presented. In FIG. 21E an Automatic augmentation of pupil 2112 coordinates superimposed on the reading test content in spatio-temporal dimensions, which will give a Dr. analyzer the movement order of the pupil is shown as an example. The doctor can accept the automatic grading or can manually enter the grading for the eye movement test.

Figure 22B:
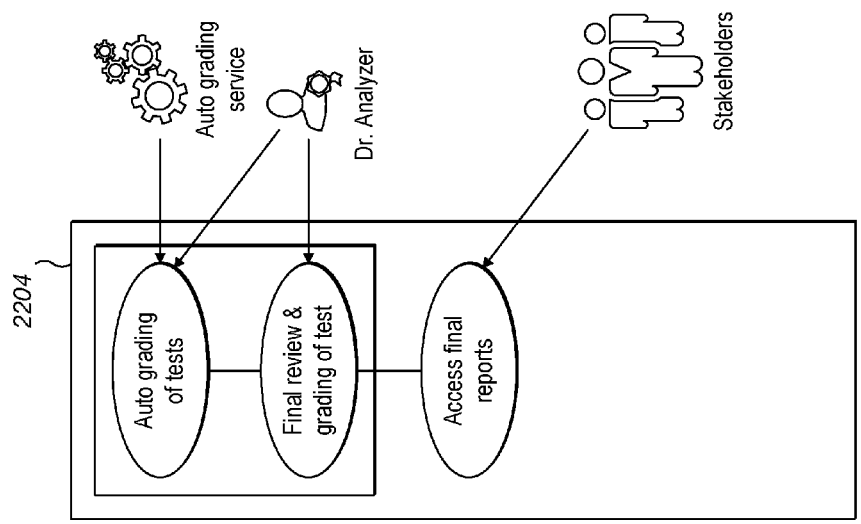
FIGS. 22A and 22B shows a use case diagram of the end to end dyslexia test system from a user (student, test admin, stakeholders, and dyslexia therapist) stand point.
Figure 22A:
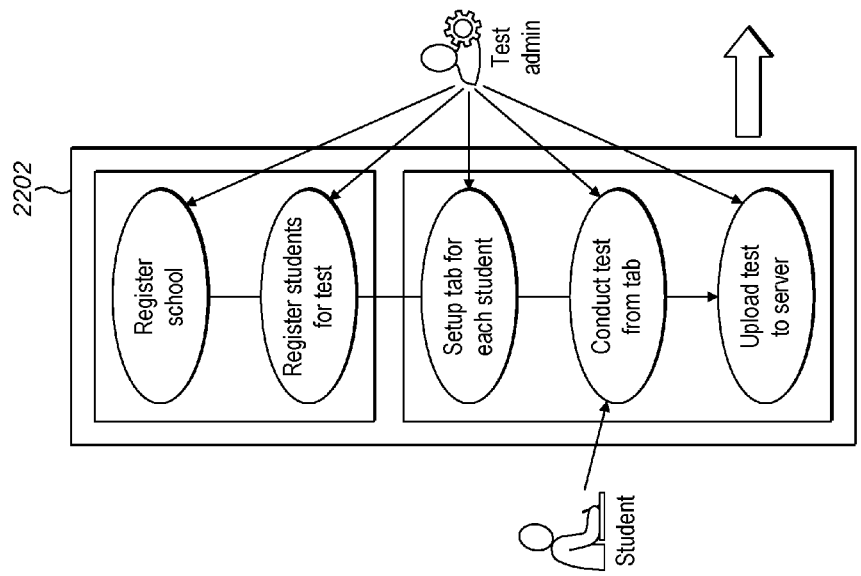

FIG. 22A illustrates the use case diagram for the user to complete the test. The registration process for the student is illustrated in 2202, where the test administrated registers the school and students. The student takes the test from the tab that has been set up by the administrator. The client component in the tab transfers the results and data to backend intelligence over cloud/Internet through network interface. In FIG. 22B the data analysis 2204 in the Dyslexia analytics system 606 goes through analysis using auto grading services and displayed as results. The final review is done through experts such as doctors and analyzers. The final reports are sent to policy handlers and stakeholders.

Figure 23A:
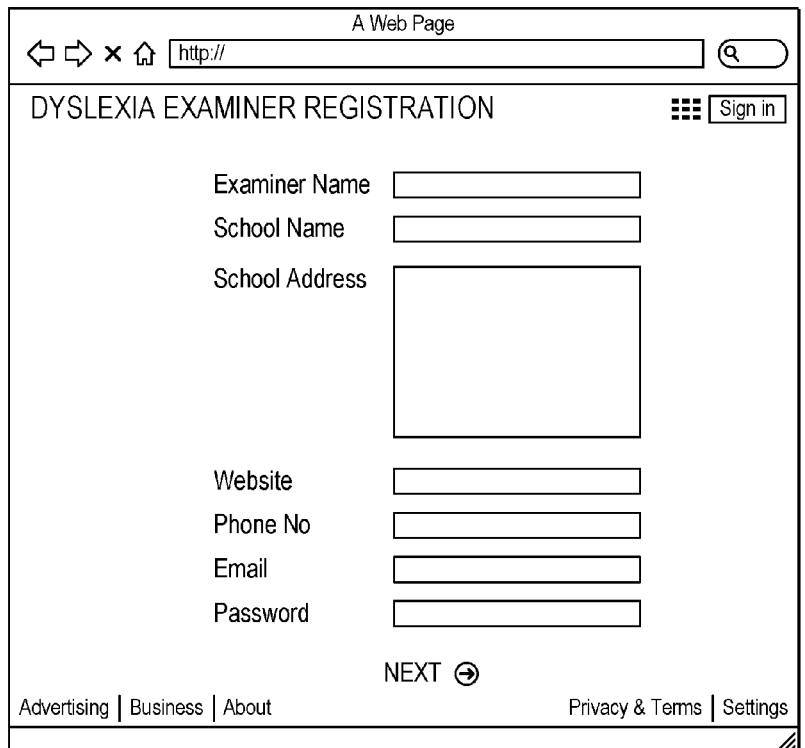
FIGS. 23A and 23B illustrate the user interface for an examiner registration and login.
Figure 23B:
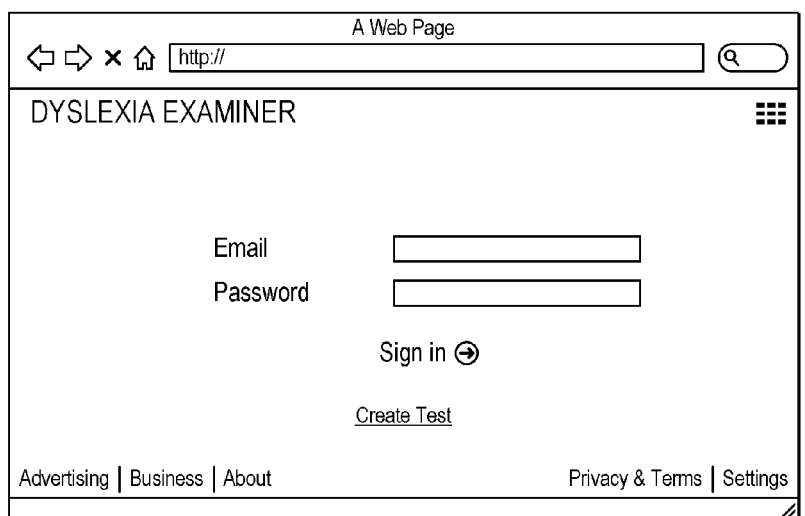

FIG. 23A illustrates examiner registration and login process. The registration 2302 is directly authenticated at the backend intelligence system. In FIG. 23B is shown that the user name and password is verified in a secure fashion directly over network interface. This ultimately has to meet the HIPPA rules of United States for privacy and individual medical records protection as well.

Figures 24A, 24B:
FIGS. 24A, 24B and 24C illustrate the user interface for a student or user registration and login.
Figure 24C:
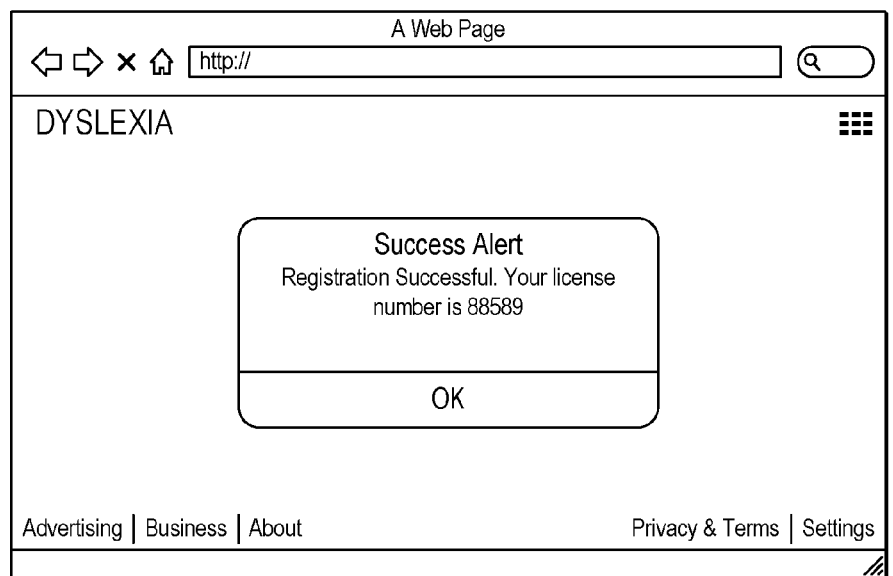

FIG. 24A illustrates the school registration process 2402, student registration process 2404, in FIG. 24B, and the authentication 2404, in FIG. 24C, by the administrator before the student takes the test.

Figure 25B:
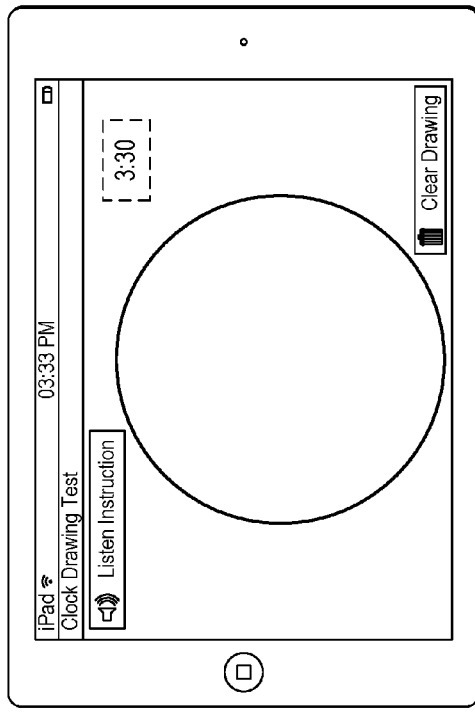
FIGS. 25A, 25B, 25C, 25D, 25E and 25F illustrate the dyslexia test module stages for users above age 10.
Figure 25A:
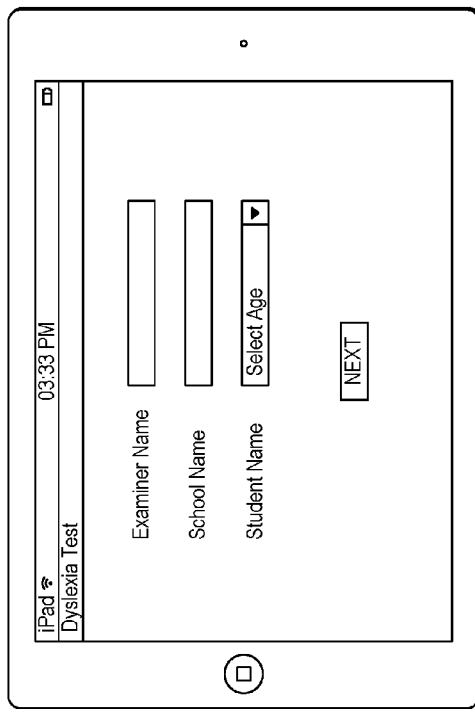
Figure 25D:
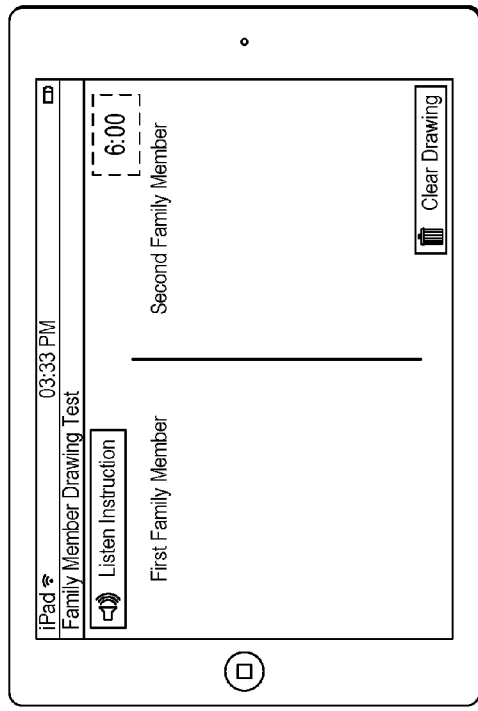
Figure 25C:
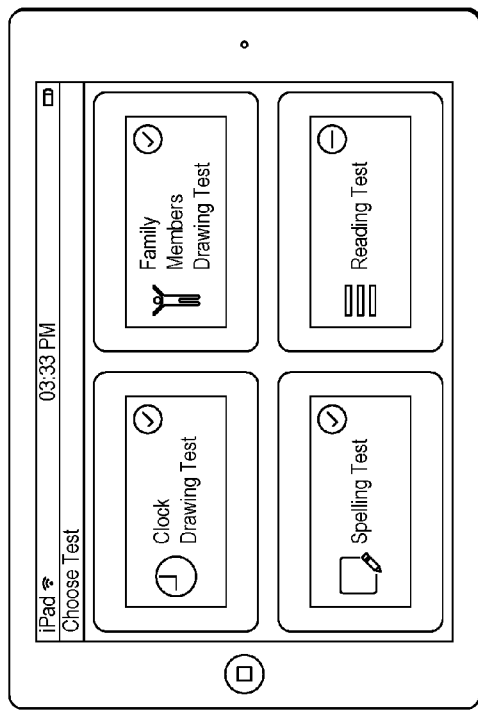
Figure 25F:
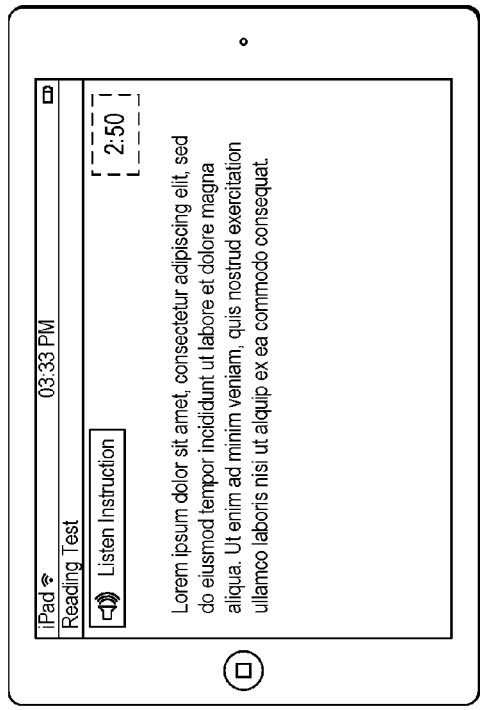
Figure 25E:
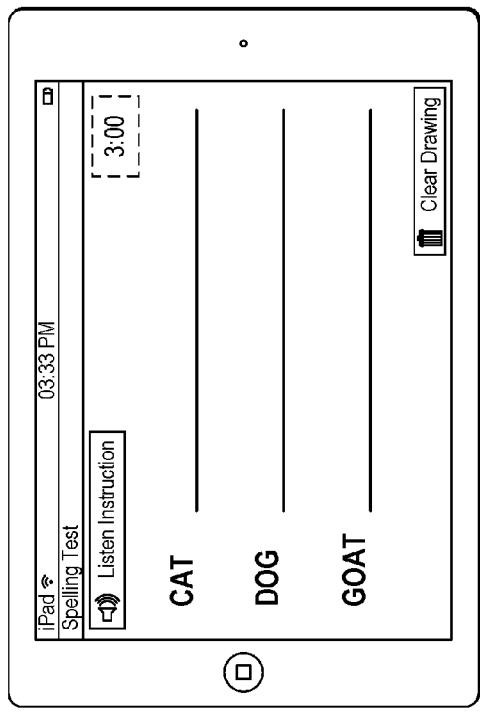

FIG. 25A illustrates the dyslexia test module procedure for ages 10 and above. The authentication 2502 is followed by the administration of the four tests 2504 (FIG. 25C shows the choices a user can make before they start the test). Each test has timeline as shown in 2506. After the administration of the clock test 2512 (shown in FIG. 25B), spelling test 2506 (FIG. 25E), reading test 2516 (FIG. 25F) and family member drawing test 2514 (FIG. 25D), the data is submitted to Dyslexia analytics system.

Figure 26B:
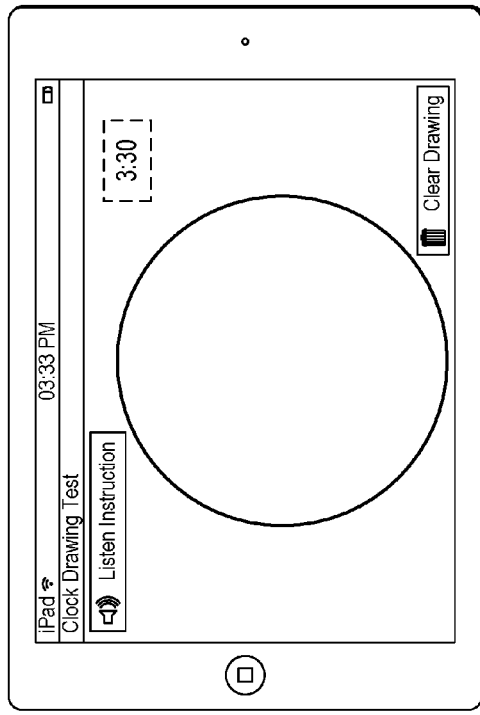
FIGS. 26A, 26B, 26C and 26D illustrate the dyslexia test module for younger kids.
Figure 26A:
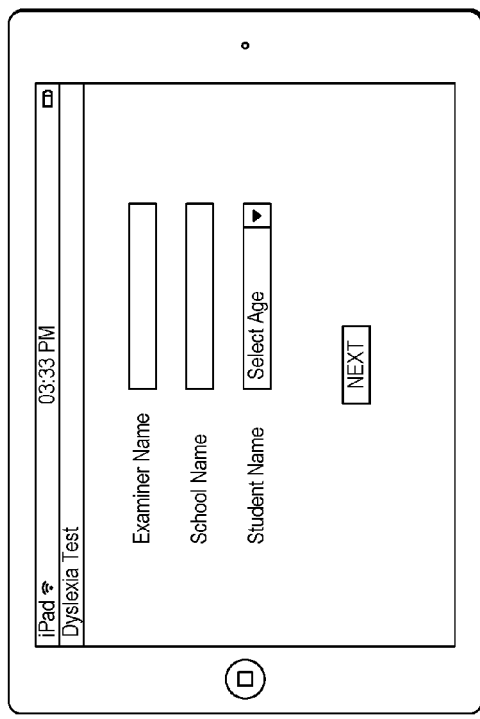
Figure 26D:
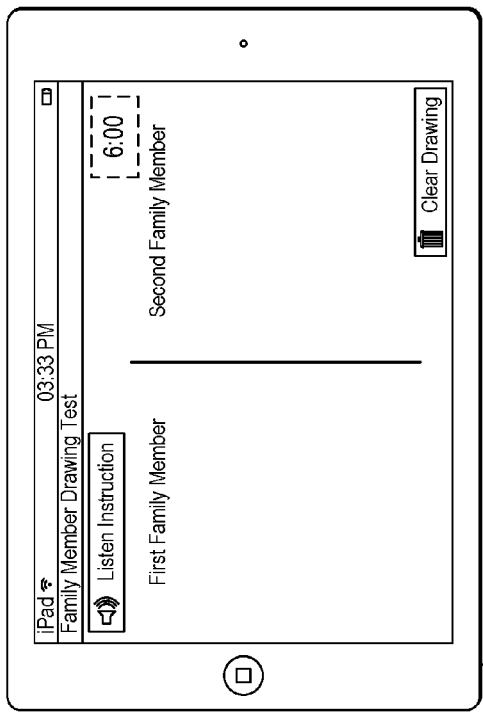
Figure 26C:
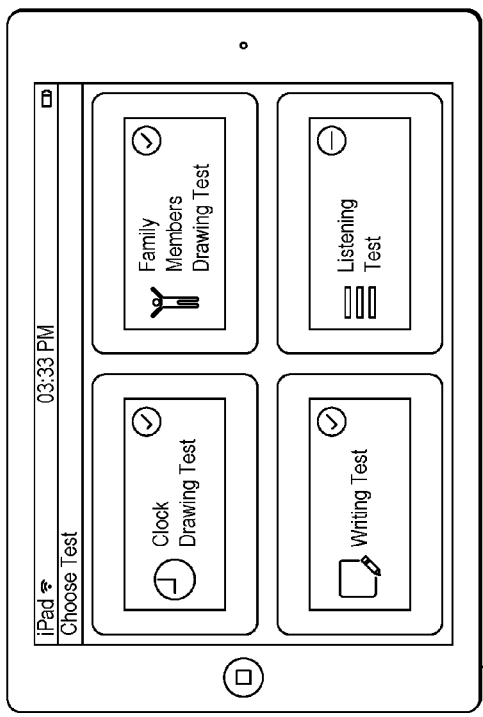

FIG. 26A illustrates the dyslexia test for young kids, where the authentication 2602 is administered followed by the four tests 2604 (FIG. 26C). The tests are simpler compared to those of age 10 and above. FIG. 26B shows Clock drawing is 2612 which is simpler. The writing test 2606 is confined to alphabet repetition. FIG. 26D actually provides space for a drawing test.

Figure 27A:
FIGS. 27A and 27B illustrate the dyslexia test module user interface for doctors and experts to register and login.
Figure 27B:
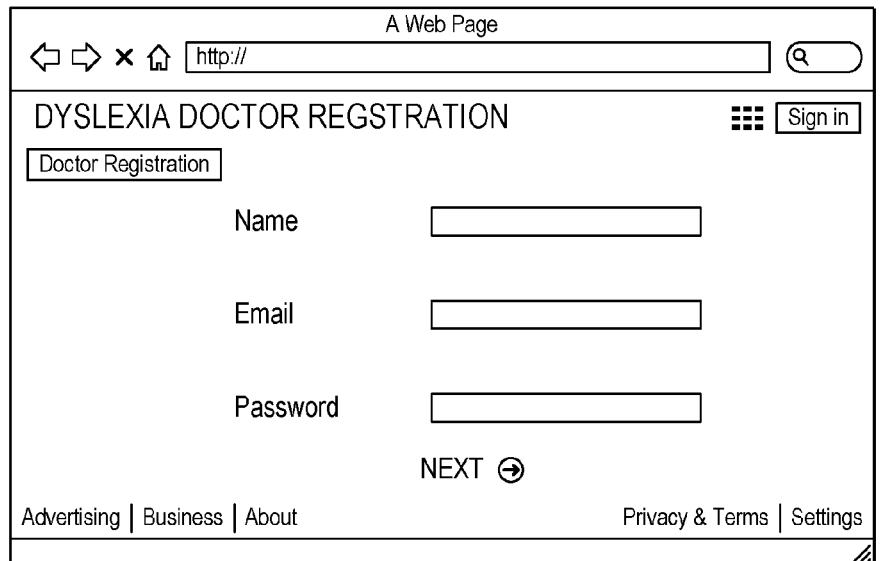

FIG. 27A illustrates the experts and doctors registration and login process. Doctor registration 2702 and login 2704 (FIG. 27B) are authenticated by the administration modules in the backend intelligence system 606.

Figure 28A:
FIGS. 28A and 28B illustrate the test result dashboard for an expert and doctor for examination of analysis and results.
Figure 28B:

FIG. 28A illustrates the test result dashboard at visual interface 708. The dashboard for the doctor provide various schools and communities 2802 and on choice of a school or community various users, students and individuals are listed 2804 (FIG. 28B) with their respective performance analyzed through intelligence engine and doctors input.

Figure 29:
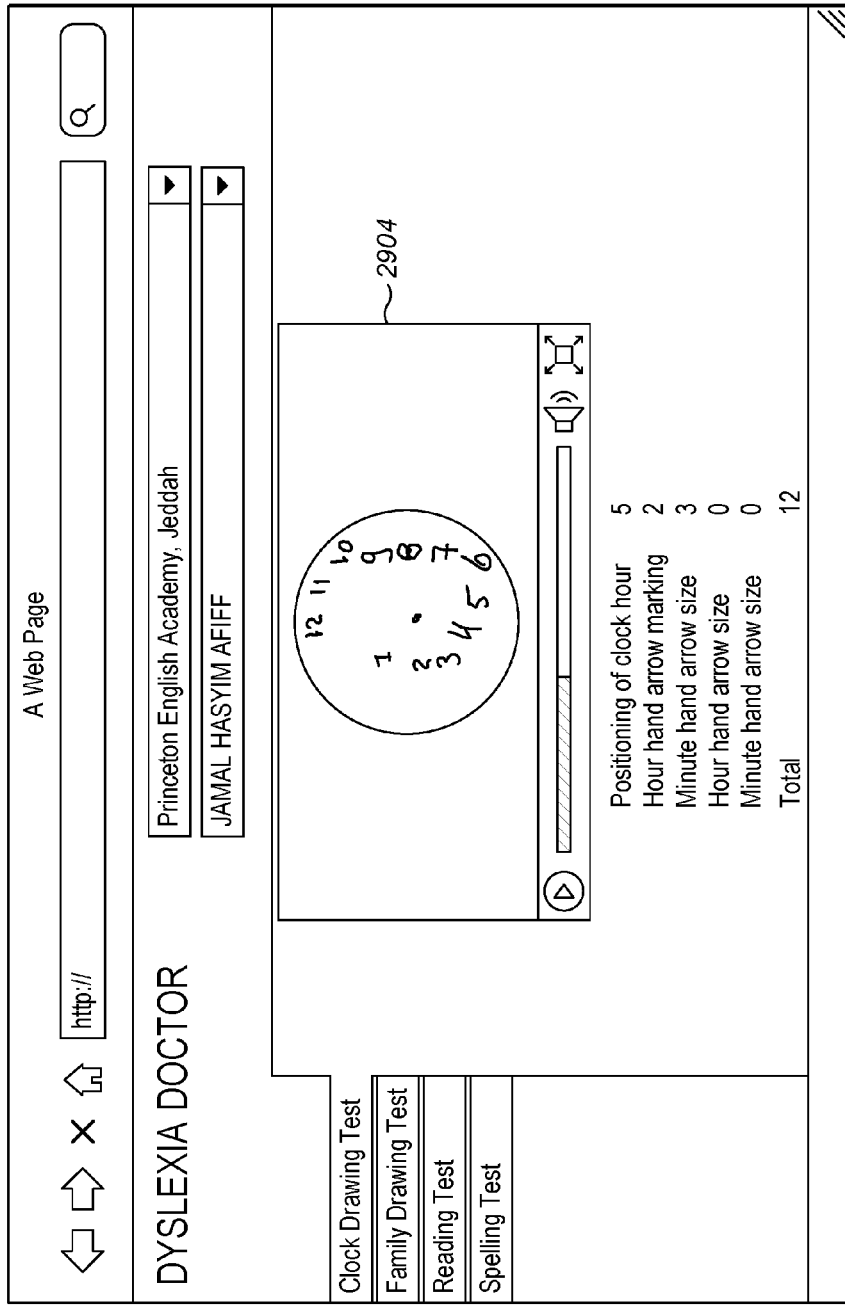
FIG. 29 illustrates the user interface view for an expert or a doctor for clock drawing test result. The interface shows automatic grading by considering possible dyslexic pattern observed from the video and stylus pen movements.

FIG. 29 illustrates the dyslexia test result for clock drawing test 2902 for an individual user as seen from the visual interface 708 of doctor for further analysis.

Figure 30:
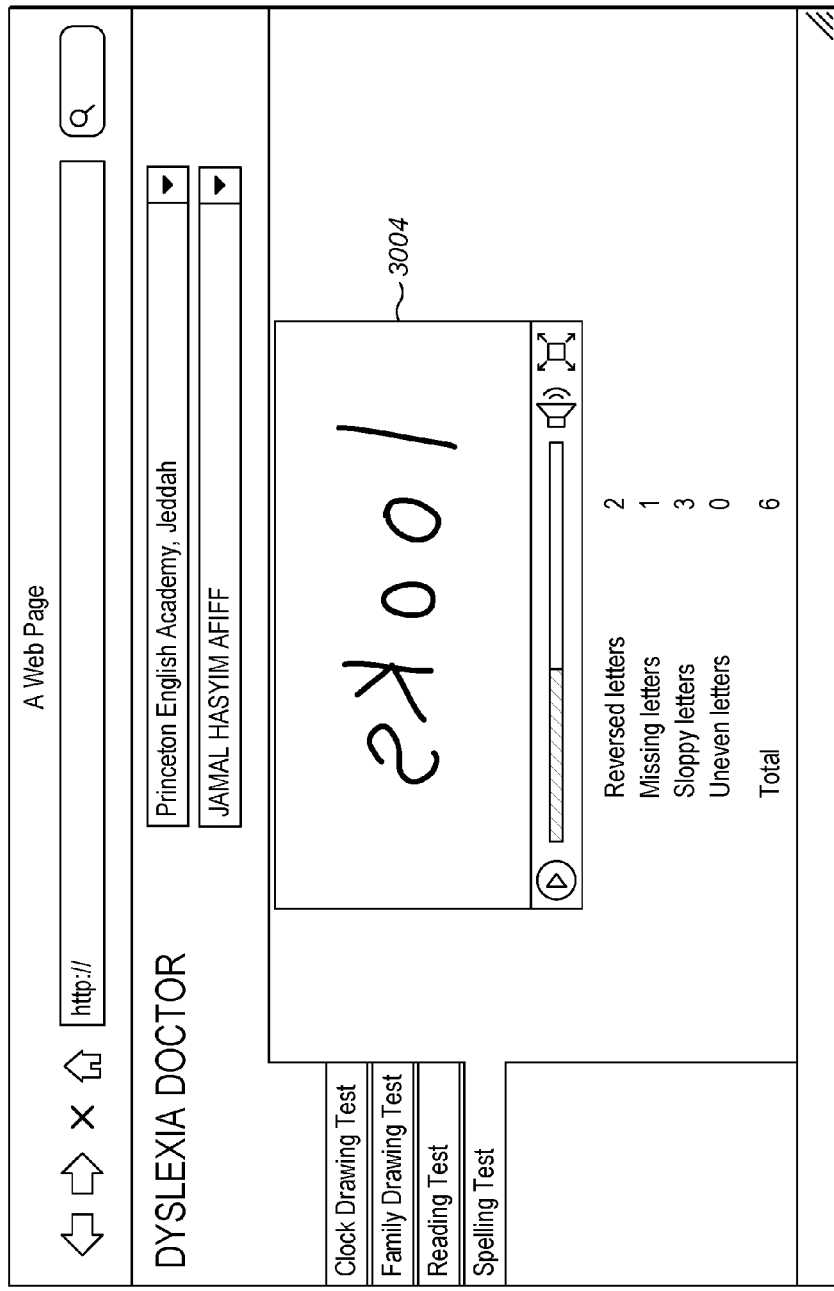
FIG. 30 illustrates the user interface view for an expert or a doctor for spelling test result. The interface shows automatic grading by considering possible dyslexic pattern observed from the video and stylus pen movements.

FIG. 30 illustrates the spelling test result 3002 as seen by visual interface 708 seen by the doctor. The individual data 3004 is clearly shown as captured by the client component.

Figure 31A:
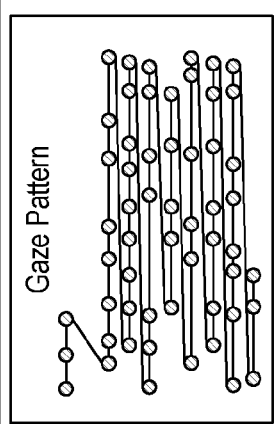
FIGS. 31A, 31B and 31C illustrate the user interface view for an expert or a doctor for viewing the reading test result. The result shows normal and recorded results for comparison. The interface shows automatic grading by considering possible dyslexic pattern observed from the video and pupil movement trails superimposed on the actual text. It also allows manual grading of the reading test.
Figure 31B:
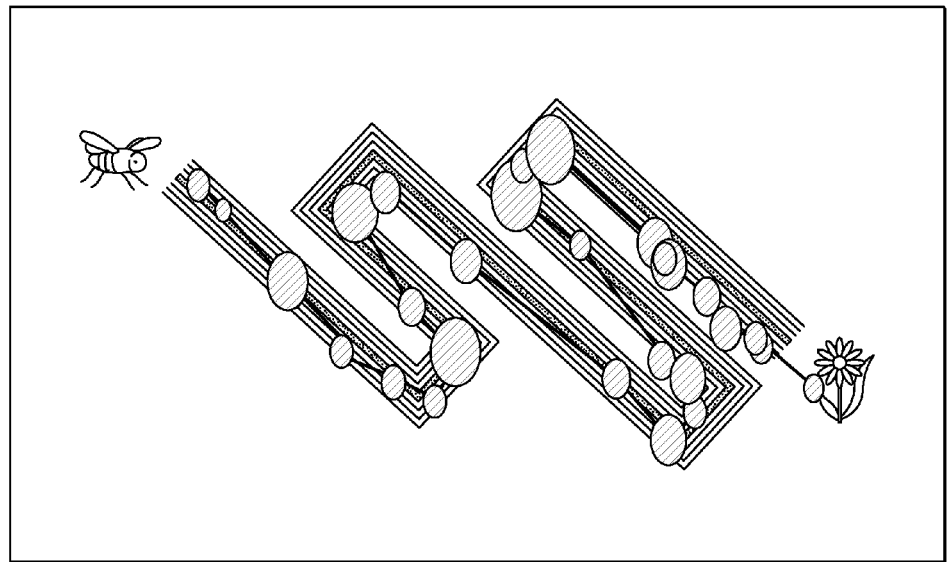
Figure 31C:
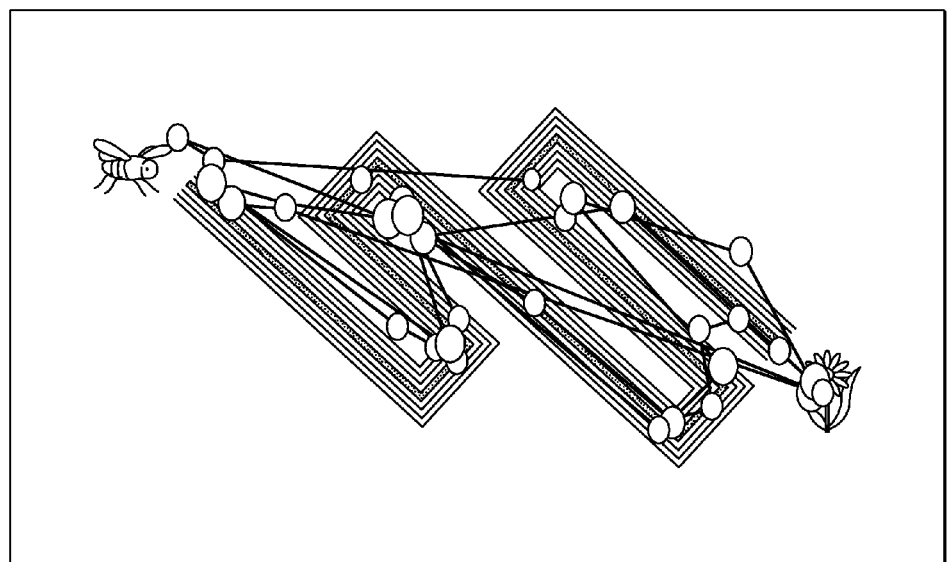

FIG. 31A illustrates the reading test result for an individual 3102. In FIG. 31B and FIG. 31C, the normal pattern of pupil movement is shown 3104 and compared to the captured pupil movement 3104 the examined user or student.

While the user reads the text, the pupil tracker reads the pupil movement co-ordinates and stores in a temp file. Once the reading module is finished, this X, Y values are sent to the server side API. The server side API simply plots the X, Y values and makes a JPG file, which will be made available to the doctor's module (same like we show the video for other three modules). Once plotted, the patterns should look like a continuous z pattern as following. Once the pupil coordinates are sent from the tab to the server, a server function receives the excel or csv or json file, passes it to the plotting function, returns a JPG image and stored in the web server folder, which is shown in the respective reading test web page in the doctor module. Not only this image is made available for the doctor to manually observe the dyslexic eye pattern, but also a new audio module is introduced where the audio is also be captured. It means, when the student looks at the text and read aloud (he/she has to read it loudly while he reads the text by eye movement). At the end of the test, both pupil movement coordinates and audio is stored and made available at the server side doctor module. The doctor now can see the pupil plot superimposed on the text he/she read and hear the audio.

In one embodiment, FIG. 31 has the following methodology for reading module:
  User puts correct license code and open the app
  User chooses Reading module and language
  Timer starts counting T minutes.
  User starts reading texts with eye and loudly using voice from left (non-Arabic) or from right (Arabic)
    i) CaptureVoice function captures the audio stream and stores in a temporary file
    ii) CapturePupilCoordinate function captures pupil coordinates 3102 and stores in a temporary file
    iii) a timer and normalized aspect ratio is used to synchronize the reading text location and pupil movement and make them augmentable and make the pupil coordinate superimposed on top of the text 3102.
  User clicks on done or the timer expires
  A session multimedia file along with user profile is created that contains the synchronized text, audio and pupil movement data, which is ready for uploading to the server.

Figure 32:
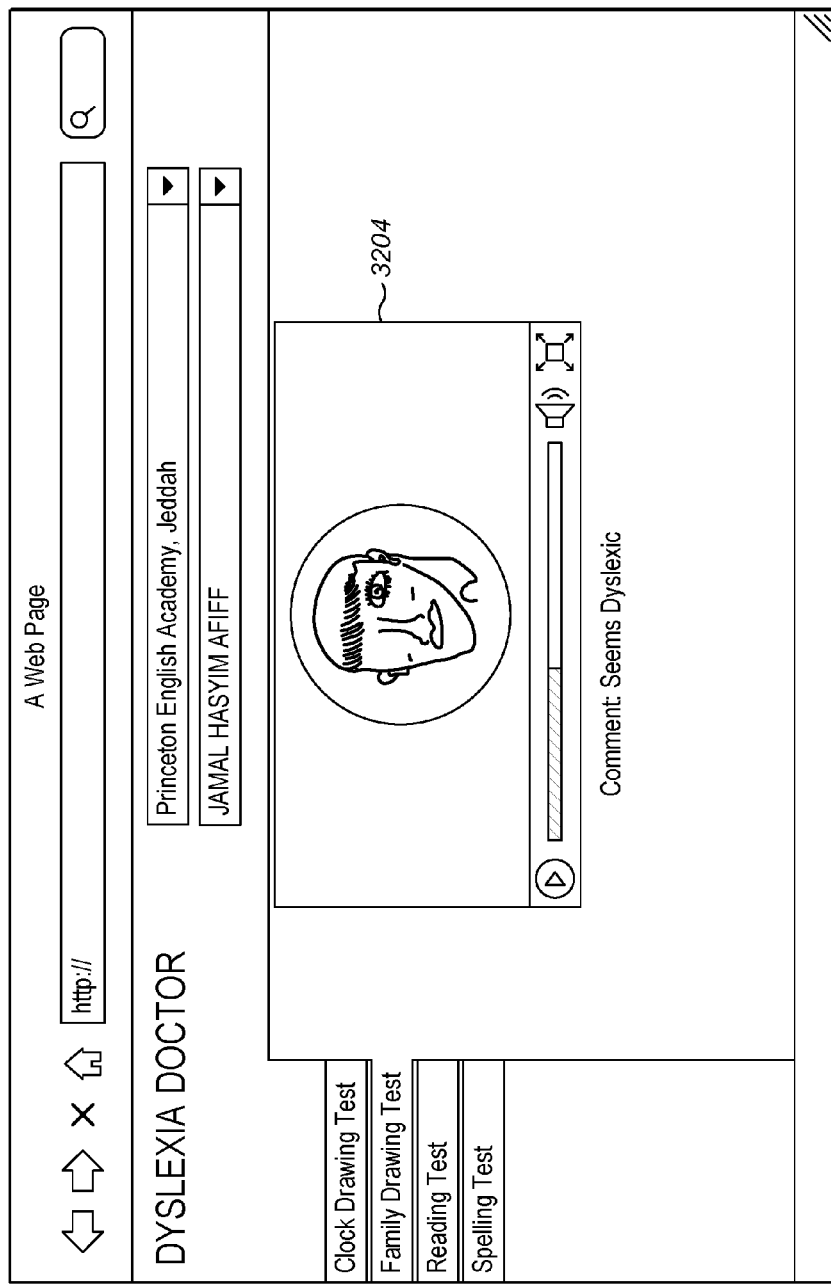
FIG. 32 illustrates the user interface view for an expert or a doctor for viewing the family member drawing test result. The interface shows automatic grading by considering possible dyslexic pattern observed from the video and stylus pen movements.
Figure 33:
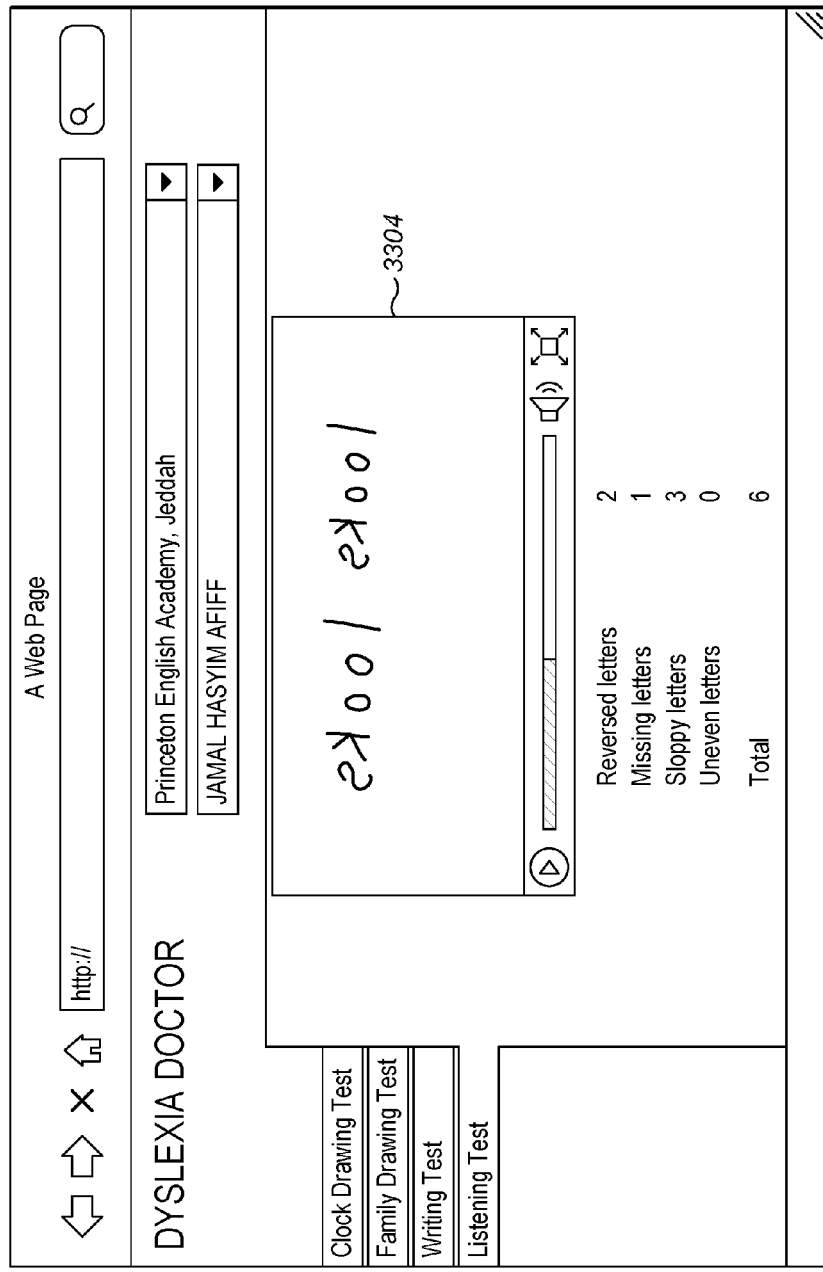
FIG. 33 illustrates the user interface view for an expert or a doctor for viewing the listening test result.
Figure 34:
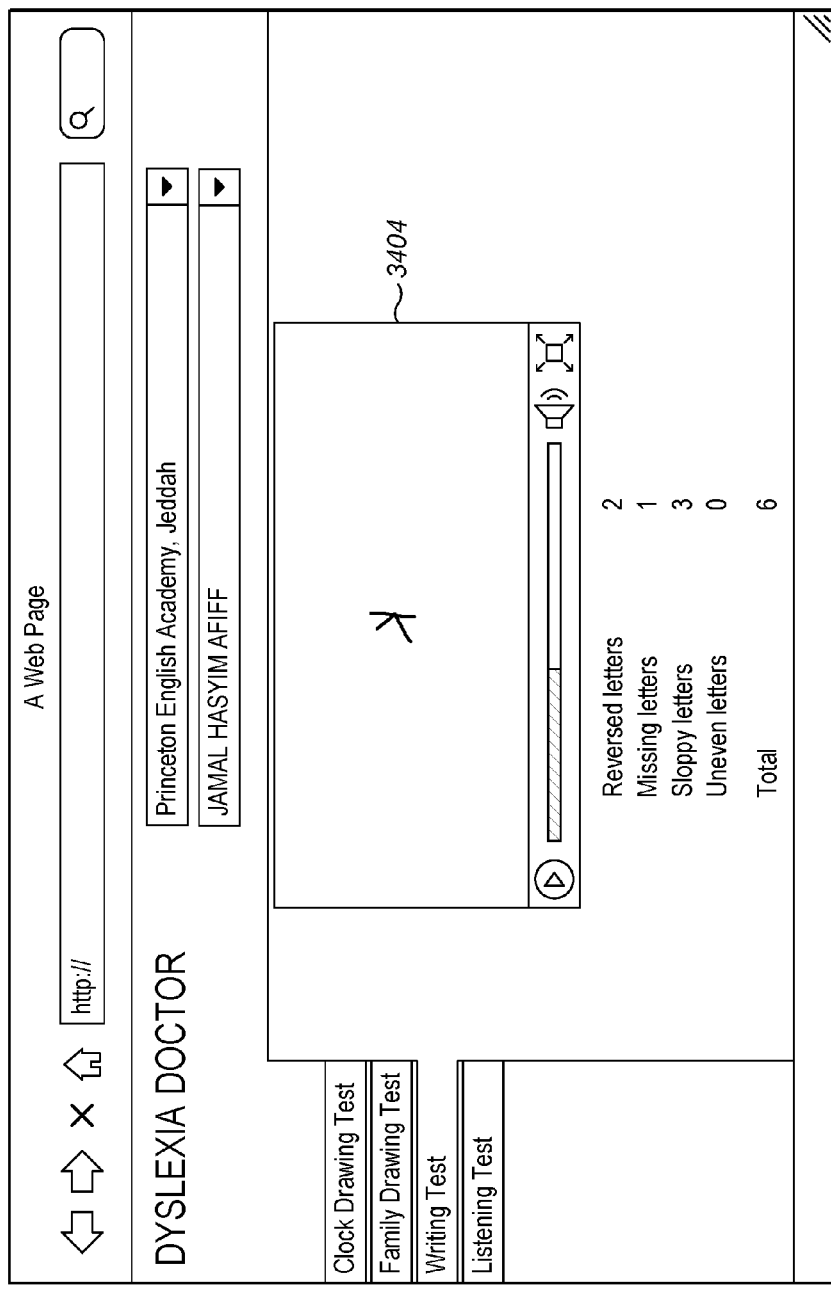
FIG. 34 illustrates the user interface view for an expert or a doctor for viewing the letter writing test result.

FIG. 32 illustrates the drawing family member test result as seen by the dyslexia doctor 3202. The data for the user 3204 as captured by the client component is shown in the visual interface of doctor 708 for further analysis. FIG. 33 illustrates the listening test result of an individual or student 3302 as captured by the client component 3304. This is displayed in visual interface 708 so doctor or expert can further analyze it. FIG. 34 illustrates the letter writing test result of an individual or student 3402 as captured by the client component 3402. The data 3404 is reviewed by the doctor through visual interface 708 for further analysis.

Figure 35:
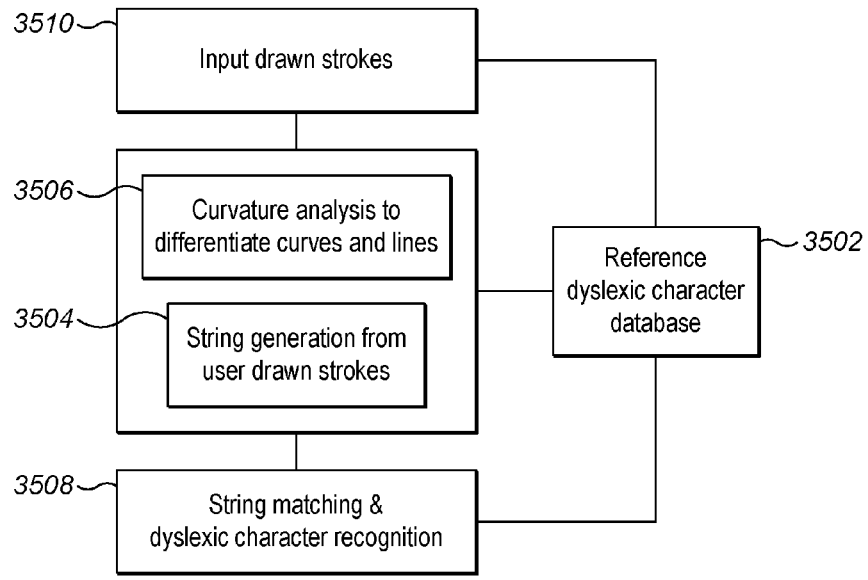
FIG. 35 illustrates the system organization of the proposed methodology.

FIG. 35 illustrates the system organization and the mathematical foundation of the proposed dyslexic writing pattern detection method. FIG. 35 depicts a high-level overview of our proposed dyslexic character recognition system, which consists of four main components. In the reference dyslexic characters database component 3502, individual characters, provided by different dyslexic patterns of characters available from Dr. analyzer 3510, are scanned, pre-processed and then stored in the reference characters' database as 48×48 matrix format. In stroke generation component 3504, the reference character is broken into its primitive strokes such as curves and straight lines. The curvature analysis and string generation component 3506 implements curvature analysis methodology to differentiate between curves and lines and generates the appropriate string consisting of numeric codes of each stroke that uniquely identifies a character from its structural representation. Finally, the string matching and character recognition component 3508 applies the dynamic programming paradigm to recognize the character.

Figure 36:
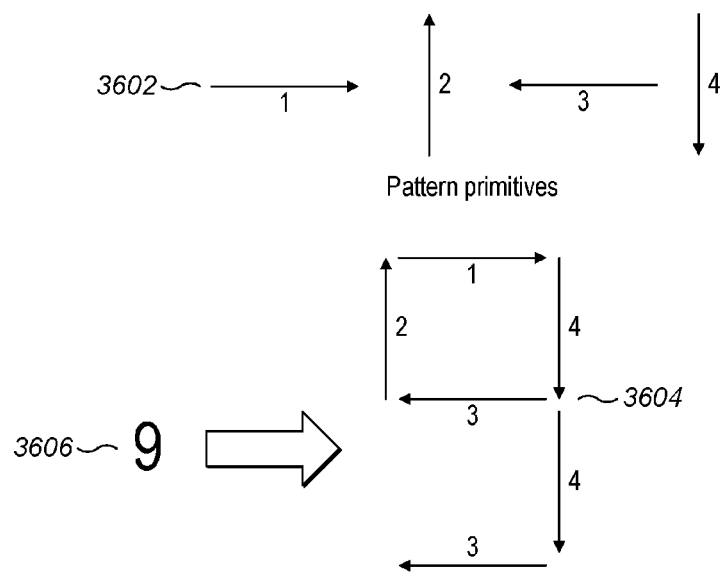
FIG. 36 illustrates a numeral broken down into primitives for proper identification.

FIG. 36 illustrates the methodology that takes the image containing the letters 3606 and breaks down each number and letters 3604 into its primitives 3602. The Figure captures the input and preprocessing. The captured stroke image file containing test characters is either enhanced/compressed or restored to form a 48×48 pixel size image. Once stored in the cloud database, the process proceeds by scanning alternately from left to right and from top to bottom along various rows and columns of the input array. This continues until a black byte is encountered. A byte is taken as black if it has more than one black point.

To recognize a given dyslexic pattern within a typed character, the character needs first to be digitized into a matrix of binary format for ease of handling. The digitizer methodology converts a physical sample to a pattern vector as following: $X=[X1\ X2\ X3\ \ldots\ Xn]$. Where n is the number of measurements. Component $Xi$ of the vector $X$ assumes the value 1 or 0 depending on the state of the i-th position for a particular input. The representation is in the form of a matrix, whose entries have one of the two values 0 (Zero) or 1 (One) corresponding to white and black points in the original image respectively.

Figure 37:
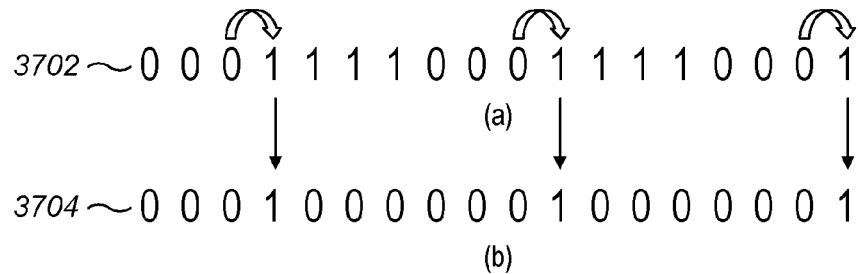
FIG. 37 illustrates the two scenarios before and after contour tracing.

FIG. 37 illustrates the contour tracing and filtering methodology. Contour tracing is the process of finding a series of black points on the boundary of a black region in a white field. The white to black transition points of the letter are obtained by scanning the digitized character from left to right and from top to bottom each time and storing the obtained values in a memory location. The zero (0) to one (1) transition 3702 and contour traced output 3704 are shown. The next task towards dyslexic pattern recognition is to filter out all the isolated 1's (ones), called stray points, which are presented in the contour map of the character to be recognized. These stray points are those that are not associated with the alphabet or letter; however, they might be generated by stylus pane mistakenly touching the tablet window during the writing process and must be eliminated before the actual dyslexic recognition process starts. During the filtering process, a '1' is considered to be isolated if there is no similar '1' in its neighborhood region, defined as seven digits above and below the row of the reference digit.

Figure 38:
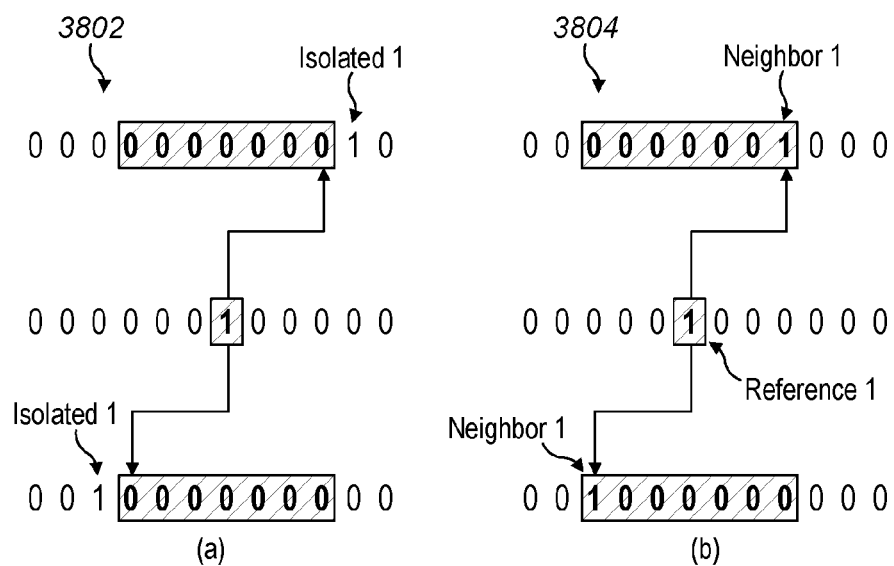
FIG. 38 illustrates the filtering process.

In FIG. 38, the middle row corresponds to the reference binary 1 under consideration. Both digits '1' in the upper and lower rows 3802 are not neighbours of the reference digit '1' because they do not lie within the seven digits region. Both upper and lower row 1's are recognized as neighbours of the reference digit 3804. Therefore, we keep them in the matrix. The process of filtering out unneeded digits is performed by applying the binary operator 'And' for each byte with the mask of its top and bottom bytes then applying the 'Or' binary operator on the computed results. The resulting value is stored in the matrix. For the first and last lines of the matrix, only the bottom and the top bytes are taken respectively since neither the first line is bordered by a line above it nor the last line by one below it.

FIG. 38 also illustrates the Strokes Extraction Process methodology. To extract the drawn dyslexic character strokes, all x and y co-ordinates of each pixel in the filtered file needs to be saved to the recognition engine. As described above, the recognition process starts from the top left corner and proceeds towards the bottom in order to find continuous points. Points in a line are deemed continuous if three bits on either side in its immediate upper line are black, as depicted. If a discontinuity occurs, scanning proceeds to the next line with the assumption that the void in the current line is due to improper scanning. If the next line presents continuity, a black point is assumed in the previous line because improper scanning may result in loss of pixel and its coordinates are saved. Otherwise, the stroke is assumed to have terminated. All black points '1' of the stroke are terminated by a '0' during the storage process of the coordinates so that they are not reconsidered when the scanning process of searching for the next stroke starts again from the upper left corner. The scanning strokes process continues until no new strokes are found. The result is to produce the collection of stroke coordinates. We need this extraction process because we have to split up the image into several parts.

Figures 39, 40:
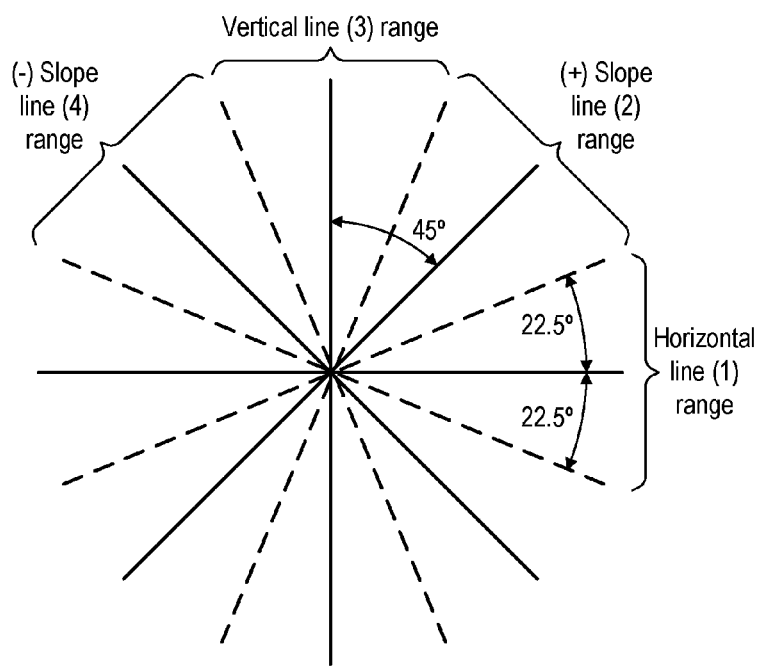
FIG. 39 illustrates the strokes used for dyslexic character recognition in the table.
FIG. 40 illustrates the ranges of the straight lines with various degree of geometric accuracy.

FIG. 39 illustrates the Strokes encoding process methodology. For the purpose of dyslexic character recognition, it is desired to generate a numeric code for each character. The first step in this procedure is the selection of strokes and the generation of code for each stroke in a character. The selection of strokes is illustrated. In our methodology, each input pattern is resolved into primitive structural elements called strokes or morphs. The first step is the selection of appropriate morphs in terms of which the dyslexic patterns of interest can be represented. To simplify the selection process, we aim at spotting strokes that are simple enough to recognize and minimum in number to be easy to find. For our purpose and analysis, six simple strokes were chosen to represent dyslexic character patterns and 10 numeric digits. These strokes are shown in FIG. 39.

FIG. 40 illustrates the wide range of deviation that is allowed in each of the six defined strokes. The intuition behind choosing these strokes is obvious since all dyslexic patterns consist of lines or curves. Though there are characters that have some form of a circle shape, this is disregarded because when we side trace the letter, we only obtain the vertical convex or vertical concave curves. So, we take those lines or curves as a principle part of the character. As a result, a wide range of deviation is allowed in each of the six defined strokes.

Finding the strokes codes is an important procedure within the methodology. The coordinates of a particular stroke are now analyzed to find the appropriate code of that stroke. The strokes under consideration are either curves or straight lines with the main assumption that the characters of any alphabet in any language can be represented by a combination of those. Later, the co-ordinates of continuous strokes are assembled together to find the appropriate numeric codes. To form an equation from some points, we set the points in the equation, then we get a path. The equation of curve fitting is $$x = a + by + cy^2 \qquad \text{Equation 1}$$

where a, b, and c are as follows:

$$a = \frac{\begin{vmatrix} \Sigma x & \Sigma y & \Sigma y^2 \\ \Sigma xy & \Sigma y^2 & \Sigma y^3 \\ \Sigma xy^2 & \Sigma y^3 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$b = \frac{\begin{vmatrix} N & \Sigma x & \Sigma y^2 \\ \Sigma y & \Sigma xy & \Sigma y^3 \\ \Sigma y^2 & \Sigma xy^2 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$c = \frac{\begin{vmatrix} N & \Sigma y & \Sigma x \\ \Sigma y & \Sigma y^2 & \Sigma xy \\ \Sigma y^2 & \Sigma y^3 & \Sigma xy^2 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

Where N=Total number of points on the stroke. The point on the stroke which has maximum curvature ($\kappa$) is calculated by using the formula $$\kappa = x_2 / (1 + x_1^2)^{3/2} \qquad \text{Equation 2}$$

Here $x_1 = dx/dy$ & $x_2 = d^2x/dy^2$

After extensive research and curve analysis we have found that if the value of $\kappa >= 0.9$, then the stroke is assumed to be a curve, otherwise (κ<0.9), it is assumed that the stroke is a straight line. This new approach in differentiating the curve and straight line based on the value of κ will result in a significant amount of error minimization and enhanced recognition as we will demonstrate later. Again, code 5 or 6 is assigned according to the value of a constant c, whether positive or negative.

The slope of each line is calculated according to the following equation $$x=a+by \qquad \text{Equation 3}$$

Transforming equation 3 to y=mx+c form, we get y=(x/b)−(a/b). So the slope of the line=1/b, where a, b are defined as follows:

$$a = \frac{\begin{vmatrix} \Sigma x & \Sigma y \\ \Sigma xy & \Sigma y^2 \end{vmatrix}}{\begin{vmatrix} N & \Sigma y \\ \Sigma y & \Sigma y^2 \end{vmatrix}} \quad b = \frac{\begin{vmatrix} N & \Sigma x \\ \Sigma y & \Sigma xy \end{vmatrix}}{\begin{vmatrix} N & \Sigma y \\ \Sigma y & \Sigma y^2 \end{vmatrix}}$$

Again, N is the number of points in a stroke (N) of a given character. If N is less than or equal to 4, the stroke code is considered to be 0. This is explained by the fact that improper touch on the tablet screen by the stylus can create up to four points. So setting that condition on the value of N makes up for this. A stroke with code '0' is created due to the existence of noise in the surrounding of the character.

The methodology to encoding the characters includes the representation of characters in the form of a numeric string. The numerals in the code not only indicate strokes which build the characters but also show the relationship among the strokes. The strokes in the characters are traversed exactly one time from left to right and from top to bottom along various rows and columns. All strokes are traversed exactly once. The letter code consists of the stroke codes written down in the order in which they were encountered. It is possible to get an idea about the structure of the character from its code. The methodology starts scanning process from the top left corner and stopped at the bottom right corner.

Figures 41, 42:
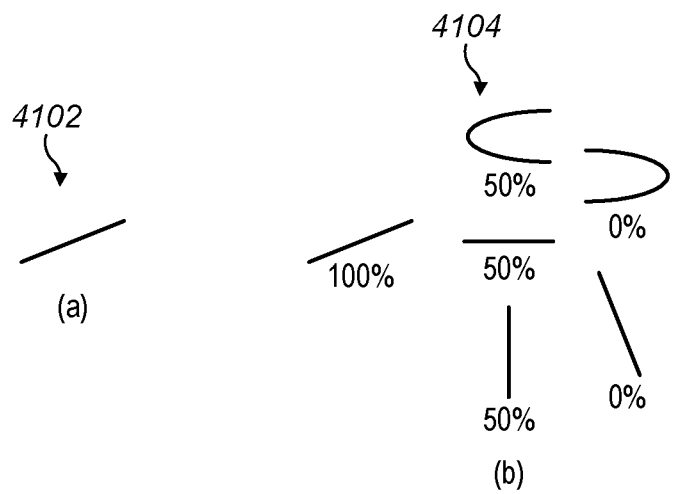
FIG. 41 illustrates the reference segments and matching scores as part of recognition.
FIG. 42 illustrates the matching matrix.

FIG. 41 illustrates the recognition of characters using matching scores. The characters represented by numeric string codes are now ready to be recognized. A search is conducted on a dictionary of codes called reference strings to find a matching code corresponding to that generated from the input character. The reference segment and the matching scores for the corresponding input segments are shown in FIG. 41. Reference segment 4102 and the corresponding possible input segments 4104 are illustrated.

FIG. 42 illustrates the methodology for matching matrix. In this process, the reference pattern is thought of as a sequence of segments. In order to compare it with the input string, we need a reference string. We represent the reference string R by $$R=\{Rseg_1,Rseg_2,\ldots,Rseg_k\} \qquad \text{Equation 3}$$

Whereas the input string I, which is also a list of segments is represented by $$I=\{Iseg_1,Iseg_2,\ldots,Iseg_n\} \qquad \text{Equation 3}$$

FIG. 42 is of a matching matrix that we have included to 'weigh' the minimum score the input deserves. The matrix's rows are referenced by the input segments, the columns by the reference segments since we must compare with previous data. The intersection of the i-th input segment and j-th reference segment holds the matching score between the i-th and j-th input segments. The matching matrix is shown in FIG. 42, where Si,j denotes the matching score.

FIG. 43 illustrates the relative matching scores for specified dyslexic primitive codes are shown in Table. In the methodology to compute optimal score, after we designed and built the matching matrix, optimal path is found through the matrix in order to achieve maximum dyslexic pattern recognition scores. The methodology works as follow:

If we are currently in $M_{(i,j)}$, we compute: Equation 4

$$Sl=M_{(i,j)}+\max((M_{(i+1,j)}+M_{(i+2,j)}),(M_{(i+1,j)}+M_{(i+2,j+1)}))$$

$$Sr=M_{(i,j)}+\max((M_{(i,j+1)}+M_{(i,j+2)}),(M_{(i,j+1)}+M_{(i+1,j+2)}))$$

$$Sd=M_{(i,j)}+(M_{(i+1,j+1)}+\max(M_{(i+1,j+2)},(M_{(i+2,j+2)},M_{(i+2,j+1)}))$$

Where,
Sl denotes a shift down.
Sr denotes a Shift right.
Sd denotes a Shift diagonally.
Then according to the maximum value found−max (Sl, Sr, Sd) we move down, right or diagonally along the matrix to the direction of the maximum value.

FIG. 44A illustrates the average dyslexic pattern matching score with 100% possibility 4402 and the average dyslexic pattern matching score with 62% possibility 4404 (FIG. 44B). The methodology to decision taking includes optimal score computation. After completing the optimal score computation as described above, we calculate the average score of matching the input string with each reference dyslexic pattern string. This is called the Average matching score. An average matching score ($S_{av}$) of 90% or more is the cutoff. Any outcome of $S_{av}$ is disregarded, and the character in question considered erroneous and hence cannot be recognized with the autograding methodology, which can be done using manual grading by the Dr. Analyzer. Note that the reference string (character) that gives the maximum $S_{av}$ with the input string is considered as the recognized and accepted dyslexic character.

INDUSTRIAL APPLICABILITY

Until this innovation, Dyslexia used to be a nightmare to properly detect at the age of 4 or 5 when a child starts going to school. Since these gifted children have difficulty in reading, writing, and drawing, they fail to properly follow the class lectures, prepare homework and write exams. Hence, the dyslexic kids starts getting isolated from the others, gets bad grades, drops out and cannot take part in innovation and other future studies. However, if they are detected in early stage, this can be addressed through assistive technologies and they can take part in regular schools. Although some single modality of screening dyslexia is available, none is available that can be applied to a mass level such as city or country or world. Hence, our proposed innovation can provide screening tests for the whole world as it is based on cloud and independent of languages. There are very significant application and superior benefits for calculating health metrics to improve for an individual. More specifically the present invention describes a more effective method and system for obtaining data regarding a user's dyslexic activity and interactions, and a novel method and system for processing such data using system templates to generate timely, accurate, relevant and actionable analytic metrics that participants, doctors and policy makers can use to guide them towards better treatments and outcomes. This technology may be used for other applications but not limited to, such as product launch, patient feedback, and customer need evaluation etc.

In addition, it will be appreciated that the various operations, processes, apparatuses and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:

1. A system for Dyslexia management, comprising:
a hardware, a network, a database, a server and a processor for implementing the Dyslexia management system;
the processor or the server further comprising:
a test module that is multilingual, to be presented to an user as consisting of tests to detect their reading, writing, drawing, spelling and listening skills in a language of the user's choice;
an intelligent dyslexia analytic module to analyze a result of the test module using several equations for a group, community and an individual wherein the several equations are Equations 1-4 in sequence, wherein Equation 1 is:
$x = a + by + cy^2$, where a, b, and c are as follows:

$$a = \frac{\begin{vmatrix} \Sigma x & \Sigma y & \Sigma y^2 \\ \Sigma xy & \Sigma y^2 & \Sigma y^3 \\ \Sigma xy^2 & \Sigma y^3 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$b = \frac{\begin{vmatrix} N & \Sigma x & \Sigma y^2 \\ \Sigma y & \Sigma xy & \Sigma y^3 \\ \Sigma y^2 & \Sigma xy^2 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$c = \frac{\begin{vmatrix} N & \Sigma y & \Sigma x \\ \Sigma y & \Sigma y^2 & \Sigma xy \\ \Sigma y^2 & \Sigma y^3 & \Sigma xy^2 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

Equation 2 is: $\kappa = x_2(1 + x_1^2)^{3/2}$ where $x_1 = dx/dy$ & $x_2 = d^2x/dy^2$ Wherein equation 3: $x = a + by$
$y = mx + c$ form, we get $y(x/b) - (a/b)$, so the slope of the line $= 1/b$, where a, b are defined as follows:

$$a = \frac{\begin{vmatrix} \Sigma x & \Sigma y \\ \Sigma xy & \Sigma y^2 \end{vmatrix}}{\begin{vmatrix} N & \Sigma y \\ \Sigma y & \Sigma y^2 \end{vmatrix}} \quad b = \frac{\begin{vmatrix} N & \Sigma x \\ \Sigma y & \Sigma xy \end{vmatrix}}{\begin{vmatrix} N & \Sigma y \\ \Sigma y & \Sigma y^2 \end{vmatrix}}$$

And, Equation 4

$Sl = M_{(i,j)} + \max((M_{(i+1,j)} + M_{(i+2,j)}), (M_{(i+1,j)} + M_{(i+2,j+1)}))$ $Sr = M_{(i,j)} + \max((M_{(i,j+1)} + M_{(i,j+2)}), (M_{(i,j+1)} + M_{(i+1,j+2)}))$ $Sd = M_{(i,j)} + (M_{(i+1,j+1)}) + \max(M_{(i+1,j+2)}, (M_{(i+2,j+2)}, M_{(i+2,j+1)}))$, Where,
Sl denotes a shift down,
Sr denotes a Shift right,
Sd denotes a Shift diagonally; and an analysis module to present an analyzed result for a medical professional to detect and manage Dyslexia in the user.

2. The system of claim 1, wherein the test module that is multilingual supports English and Arabic languages.

3. The system of claim 2, wherein the test module is 20-minute long and has 4 different tests: reading test, writing test, clock drawing test, and cognitive test through drawing family members, all with an eye tracking and audio capturing capabilities.

4. The system of claim 1, wherein the test module is incremental in complexity, context-aware content, time duration, cognitive challenges and school curriculum dependent.

5. The system of claim 1, further comprising:
A video module to capture user eye movements, hand movements and speech to be augmented with the test module for compiling a test score.

6. The system of claim 5, further comprising:
an auto grading module residing in the processor or server to detect a missing minute or hour hand, missing numbers, order of hours, location of hours, wrongly placed minute or hour hand, dislocated or wrongplaced hour or minute hour augment that with the test results and present the test score to a doctor or the user.

7. The system of claim 6, wherein the writing test part is recorded as a video interaction session as well so that it can be replayed at any time in future to retrace a writing technique specific for dyslexic user.

8. A process for Dyslexia management, comprising:
a user to login to a hardware that is connected with a network, database and a Dyslexia management system loaded to the processor of the hardware or the network to take a test for evaluating a condition for diagnosing symptoms for Dyslexia;
wherein the test consists of several modules for reading, writing, drawing, spelling and listening skills, family drawing, and letter writing;
a Dyslexia analytics system housed on a backend server or a processor to auto grade a test result using specific equation for a reading, writing, drawing, spelling and listening skills, family drawing, and letter writing test wherein the specific formula for interpretation and presentation of the test for module for reading, writing, drawing is done using Equations 1-4 in sequence, wherein Equation 1 is:

$x=a+by+cy^2$, where a, b, and c are as follows:

$$a = \frac{\begin{vmatrix} \Sigma x & \Sigma y & \Sigma y^2 \\ \Sigma xy & \Sigma y^2 & \Sigma y^3 \\ \Sigma xy^2 & \Sigma y^3 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$b = \frac{\begin{vmatrix} N & \Sigma x & \Sigma y^2 \\ \Sigma y & \Sigma xy & \Sigma y^3 \\ \Sigma y^2 & \Sigma xy^2 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$c = \frac{\begin{vmatrix} N & \Sigma y & \Sigma x \\ \Sigma y & \Sigma y^2 & \Sigma xy \\ \Sigma y^2 & \Sigma y^3 & \Sigma xy^2 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

Equation 2 is: $\kappa = x_2/(1+x_1^2)^{3/2}$ where $x_1 = dx/dy$ & $x_2 = d^2x/dy^2$ Wherein equation 3: $x=a+by$ $y=mx+c$ form, we pet $y=(x/b)-(a/b)$, so the slope of the line=1/b, where a, b are defined as follows:

$$a = \frac{\begin{vmatrix} \Sigma x & \Sigma y \\ \Sigma xy & \Sigma y^2 \end{vmatrix}}{\begin{vmatrix} N & \Sigma y \\ \Sigma y & \Sigma y^2 \end{vmatrix}} \quad b = \frac{\begin{vmatrix} N & \Sigma x \\ \Sigma y & \Sigma xy \end{vmatrix}}{\begin{vmatrix} N & \Sigma y \\ \Sigma y & \Sigma y^2 \end{vmatrix}}$$

And, Equation 4

$Sl = M_{(i,j)} + \max((M_{(i+1,j)} + M_{(i+2,j)}), (M_{(i+1,j)} + M_{(i+2,j+1)}))$ $Sr = M_{(i,j)} + \max((M_{(i,j+1)} + M_{(i,j+2)}), (M_{(i,j+1)} + M_{(i+1,j+2)}))$ $Sd = M_{(i,j)} + (M_{(i+1,j+1)} + \max(M_{(i+1,j+2)}, (M_{(i+2,j+2)}, M_{(i+2,j+1)}))$ Where,
Sl denotes a shift down,
Sr denotes a Shift right,
Sd denotes a Shift diagonally; and
a doctor to review the test result using a doctor analyzer screen and rendering their opinion to the user by filtering and flagging each test module that shows symptoms of dyslexia and a treatment plan for the user.

9. The process of claim 8, further comprising:
a backend intelligent server or a processor compiles all the data set from the user to show a trend in demography, genetic influence, statistical trend for the decision makers to use it for making health issue related decisions.

10. The process of claim 8, wherein the test module is 20-minute long and has 4 different tests: reading test, writing test, clock drawing test, and cognitive test through drawing family members, all with an eye tracking and audio capturing capabilities.

11. A system for Dyslexia management, comprising:
a user uses a test module housed on a server or a processor of a computer device used for logging in to take the a test for Dyslexia, wherein the test module consists of a reading, writing, drawing, spelling and listening skills, family drawing, and letter writing test;
a backend server captures the interaction of the user for a session for a given test module by capturing the interaction and video captured during the test period;
a Dyslexia analytics system housed on a backend server or a processor to auto grade a test result using specific equation and augments the video data captured during the session for the reading, writing, drawing, spelling and listening skills, family drawing, and letter writing test, wherein the specific equation for interpretation and presentation of the test for module for reading, writing, drawing is done using Equation 1, 2, 3 and 4 in sequence, wherein Equation 1 is:

$x=a+by+cy^2$, where a, b, and c are as follows:

$$a = \frac{\begin{vmatrix} \Sigma x & \Sigma y & \Sigma y^2 \\ \Sigma xy & \Sigma y^2 & \Sigma y^3 \\ \Sigma xy^2 & \Sigma y^3 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$b = \frac{\begin{vmatrix} N & \Sigma x & \Sigma y^2 \\ \Sigma y & \Sigma xy & \Sigma y^3 \\ \Sigma y^2 & \Sigma xy^2 & \Sigma y^4 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

$$c = \frac{\begin{vmatrix} N & \Sigma y & \Sigma x \\ \Sigma y & \Sigma y^2 & \Sigma xy \\ \Sigma y^2 & \Sigma y^3 & \Sigma xy^2 \end{vmatrix}}{\begin{vmatrix} N & \Sigma y & \Sigma y^2 \\ \Sigma y & \Sigma y^2 & \Sigma y^3 \\ \Sigma y^2 & \Sigma y^3 & \Sigma y^4 \end{vmatrix}}$$

Equation 2 is $\kappa = x_2(1+x_1^2)^{3/2}$ where $x_1 = dx/dy$ & $x_2 = d^2x/dy^2$ Wherein equation 3: $x=a+by$ $y=mx+c$ form, we get $y=(x/b)-(a/b)$, so the slope of the line=1/b, where a, b are defined as follows:

$$a = \frac{\begin{vmatrix} \Sigma x & \Sigma y \\ \Sigma xy & \Sigma y^2 \end{vmatrix}}{\begin{vmatrix} N & \Sigma y \\ \Sigma y & \Sigma y^2 \end{vmatrix}} \quad b = \frac{\begin{vmatrix} N & \Sigma x \\ \Sigma y & \Sigma xy \end{vmatrix}}{\begin{vmatrix} N & \Sigma y \\ \Sigma y & \Sigma y^2 \end{vmatrix}}$$

And, Equation 4

$$Sl = M_{(i,j)} + \max((M_{(i+1,j)} + M_{(i+2,j)}), (M_{(i+1,j)} + M_{(i+2,j+1)}))$$

$$Sr = M_{(i,j)} + \max((M_{(i,j+1)} + M_{(i,j+2)}), (M_{(i,j+1)} + M_{(i+1,j+2)}))$$

$$Sd = M_{(i,j)} + (M_{(i+1,j+1)} + \max(M_{(i+1,j+2)}, (M_{(i+2,j+2)}, M_{(i+2,j+1)}))$$

Where,
  Sl denotes a shift down,
  Sr denotes a Shift right,
  Sd denotes a Shift diagonally; and
  a doctor to review the test result using a doctor analyzer screen and rendering their opinion to the user by filtering and flagging each test module that shows symptoms of dyslexia and a treatment plan for the user.

12. The system of claim 11, further comprising:
  the user is asked to draw using a stylus a family member, the drawing is tracked for dyslexic pattern prediction and shown to the doctor by overlaying the correct lines over the drawn lines of the family member.

13. The system of claim 12, further comprising: an eye movement of the user is captured and used by the dyslexia analytics system to grade the test using these eye movements captured by the video.

* * * * *